(12) United States Patent
Boudreaux

(10) Patent No.: US 12,245,899 B2
(45) Date of Patent: Mar. 11, 2025

(54) SURGICAL INSTRUMENT WITH DUAL MODE END EFFECTOR AND MODULAR CLAMP ARM ASSEMBLY

(71) Applicant: Cilag GmbH International, Zug (CH)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1097 days.

(21) Appl. No.: 17/067,884

(22) Filed: Oct. 12, 2020

(65) Prior Publication Data

US 2021/0085420 A1    Mar. 25, 2021

Related U.S. Application Data

(63) Continuation of application No. 15/284,855, filed on Oct. 4, 2016, now Pat. No. 10,893,914.

(Continued)

(51) Int. Cl.
*A61B 18/14*    (2006.01)
*A61B 17/00*    (2006.01)
(Continued)

(52) U.S. Cl.
CPC .......... *A61B 90/04* (2016.02); *A61B 17/2804* (2013.01); *A61B 17/2812* (2013.01);
(Continued)

(58) Field of Classification Search
CPC .. A61B 2017/0046; A61B 2017/00464; A61B 17/2804; A61B 17/2812;
(Continued)

(56) References Cited

U.S. PATENT DOCUMENTS

| 5,322,055 A | 6/1994 | Davison et al. |
| 5,465,894 A | 11/1995 | Clark et al. |

(Continued)

FOREIGN PATENT DOCUMENTS

| CN | 1694649 A | 11/2005 |
| CN | 2820104 Y | 9/2006 |

(Continued)

OTHER PUBLICATIONS

U.S. Appl. No. 15/284,819.

(Continued)

*Primary Examiner* — Daniel W Fowler
*Assistant Examiner* — Bradford C. Blaise
(74) *Attorney, Agent, or Firm* — Frost Brown Todd LLP

(57) ABSTRACT

A first subassembly includes a body and an ultrasonic blade. A second subassembly is configured to removably couple with the first subassembly and includes a first clamp arm and a first clamp arm actuator. The first clamp arm is configured to be located on a first side of the longitudinal axis of the body, and the first clamp arm actuator is configured to be located on a second side of the longitudinal axis, when the second subassembly is coupled with the first subassembly. The third subassembly is similar to the second subassembly except that the second clamp arm of the third subassembly is configured to be located on the second side of the longitudinal axis of the body when the third subassembly is coupled with the first subassembly.

20 Claims, 14 Drawing Sheets

Related U.S. Application Data

(60) Provisional application No. 62/363,411, filed on Jul. 18, 2016, provisional application No. 62/243,189, filed on Oct. 19, 2015.

(51) Int. Cl.

| | | |
|---|---|---|
| *A61B 17/28* | (2006.01) | |
| *A61B 17/285* | (2006.01) | |
| *A61B 17/29* | (2006.01) | |
| *A61B 17/295* | (2006.01) | |
| *A61B 17/32* | (2006.01) | |
| *A61B 18/00* | (2006.01) | |
| *A61B 90/00* | (2016.01) | |

(52) U.S. Cl.
CPC ...... *A61B 17/2816* (2013.01); *A61B 17/2833* (2013.01); *A61B 17/2841* (2013.01); *A61B 17/285* (2013.01); *A61B 17/29* (2013.01); *A61B 17/295* (2013.01); *A61B 17/320092* (2013.01); *A61B 18/14* (2013.01); *A61B 18/1442* (2013.01); *A61B 18/1445* (2013.01); *A61B 90/03* (2016.02); *A61B 2017/00022* (2013.01); *A61B 2017/00026* (2013.01); *A61B 2017/00119* (2013.01); *A61B 2017/00123* (2013.01); *A61B 2017/00128* (2013.01); *A61B 2017/0046* (2013.01); *A61B 2017/00464* (2013.01); *A61B 2017/00477* (2013.01); *A61B 2017/00778* (2013.01); *A61B 2017/00818* (2013.01); *A61B 2017/2825* (2013.01); *A61B 2017/2829* (2013.01); *A61B 2017/2931* (2013.01); *A61B 2017/2933* (2013.01); *A61B 2017/2939* (2013.01); *A61B 2017/2944* (2013.01); *A61B 2017/2946* (2013.01); *A61B 2017/2947* (2013.01); *A61B 2017/320093* (2017.08); *A61B 2017/320094* (2017.08); *A61B 2017/320095* (2017.08); *A61B 2018/00178* (2013.01); *A61B 2018/0019* (2013.01); *A61B 2018/00297* (2013.01); *A61B 2018/00309* (2013.01); *A61B 2018/00345* (2013.01); *A61B 2018/00529* (2013.01); *A61B 2018/00589* (2013.01); *A61B 2018/00601* (2013.01); *A61B 2018/0063* (2013.01); *A61B 2018/00702* (2013.01); *A61B 2018/00708* (2013.01); *A61B 2018/00767* (2013.01); *A61B 2018/00875* (2013.01); *A61B 2018/00892* (2013.01); *A61B 2018/00898* (2013.01); *A61B 2018/00916* (2013.01); *A61B 2018/00922* (2013.01); *A61B 2018/00928* (2013.01); *A61B 2018/0094* (2013.01); *A61B 2018/00958* (2013.01); *A61B 2018/00988* (2013.01); *A61B 2018/00994* (2013.01); *A61B 2018/1405* (2013.01); *A61B 2018/1455* (2013.01); *A61B 2018/146* (2013.01); *A61B 2018/1467* (2013.01); *A61B 2090/035* (2016.02); *A61B 2090/036* (2016.02); *A61B 2090/0427* (2016.02); *A61B 2090/0436* (2016.02); *A61B 2090/0472* (2016.02); *A61B 2090/0481* (2016.02); *A61B 2090/064* (2016.02); *A61B 2090/0803* (2016.02); *A61B 2090/0808* (2016.02); *A61B 2090/0811* (2016.02); *A61B 2090/0812* (2016.02); *A61B 2090/0813* (2016.02); *A61B 2090/0814* (2016.02)

(58) Field of Classification Search
CPC ............ A61B 17/2816; A61B 17/2841; A61B 17/2909; A61B 2017/2919; A61B 2017/2932; A61B 17/320092; A61B 2017/320093; A61B 2017/320094; A61B 2017/320095; A61B 2018/00994; A61B 18/1442; A61B 18/1445
See application file for complete search history.

(56) References Cited

U.S. PATENT DOCUMENTS

| | | |
|---|---|---|
| 5,556,404 A | 9/1996 | Belanger et al. |
| 5,607,094 A | 3/1997 | Clark et al. |
| 5,797,939 A | 8/1998 | Yoon |
| 5,827,299 A | 10/1998 | Thomason et al. |
| 5,873,873 A | 2/1999 | Smith et al. |
| 5,980,510 A | 11/1999 | Tsonton et al. |
| 6,325,811 B1 | 12/2001 | Messerly |
| 6,454,781 B1 | 9/2002 | Witt et al. |
| 6,773,444 B2 | 8/2004 | Messerly |
| 6,783,524 B2 | 8/2004 | Anderson et al. |
| 7,267,677 B2 | 9/2007 | Johnson et al. |
| 7,563,269 B2 | 7/2009 | Hashiguchi |
| 8,182,501 B2 | 5/2012 | Houser et al. |
| 8,357,158 B2 | 1/2013 | McKenna et al. |
| 8,461,744 B2 | 6/2013 | Wiener et al. |
| 8,591,536 B2 | 11/2013 | Robertson |
| 8,623,027 B2 | 1/2014 | Price et al. |
| 8,652,132 B2 | 2/2014 | Tsuchiya et al. |
| 8,845,667 B2 | 9/2014 | Cruz Hernandez et al. |
| 8,974,447 B2 | 3/2015 | Kimball et al. |
| 8,986,302 B2 | 3/2015 | Aldridge et al. |
| 9,023,071 B2 | 5/2015 | Miller et al. |
| 9,060,770 B2 | 6/2015 | Shelton, IV et al. |
| 9,084,878 B2 | 7/2015 | Kawaguchi et al. |
| 9,095,367 B2 | 8/2015 | Olson et al. |
| 9,375,255 B2 | 6/2016 | Houser et al. |
| 9,381,058 B2 | 7/2016 | Houser et al. |
| 9,393,037 B2 | 7/2016 | Olson et al. |
| 9,402,679 B2 | 8/2016 | Ginnebaugh et al. |
| 9,480,466 B2 | 11/2016 | Van De Weghe et al. |
| 9,610,115 B2 | 4/2017 | Rothweiler et al. |
| 9,770,286 B2 | 9/2017 | Kase |
| 9,782,214 B2 | 10/2017 | Houser et al. |
| 9,901,754 B2 | 2/2018 | Yamada |
| 9,993,260 B2 | 6/2018 | Stokes et al. |
| 10,004,528 B2 | 6/2018 | Faller et al. |
| 10,172,636 B2 | 1/2019 | Stulen et al. |
| 10,231,782 B2 | 3/2019 | Nau, Jr. |
| 10,258,404 B2 | 4/2019 | Wang |
| 10,893,914 B2 * | 1/2021 | Boudreaux ........ A61B 17/2804 |
| 2004/0093020 A1 | 5/2004 | Sinton |
| 2004/0193199 A1* | 9/2004 | Hashiguchi .... A61B 17/320092 606/169 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0255130 A1 | 10/2009 | Jalmberger |
| 2010/0063525 A1 | 3/2010 | Beaupre et al. |
| 2010/0331873 A1 | 12/2010 | Dannaher et al. |
| 2012/0116265 A1 | 5/2012 | Houser et al. |
| 2013/0245421 A1* | 9/2013 | Andrus ............. A61B 17/50 600/409 |
| 2013/0303949 A1* | 11/2013 | Kawaguchi .......... A61B 17/282 601/2 |
| 2013/0345732 A1 | 12/2013 | Dannaher et al. |
| 2014/0135804 A1 | 5/2014 | Weisenburgh, II et al. |
| 2014/0330298 A1 | 11/2014 | Arshonsky et al. |
| 2015/0080925 A1 | 3/2015 | Schulte et al. |
| 2015/0196782 A1 | 7/2015 | Akagane |
| 2015/0313667 A1 | 11/2015 | Allen, IV |
| 2017/0105755 A1 | 4/2017 | Boudreaux et al. |
| 2017/0105757 A1 | 4/2017 | Boudreaux et al. |
| 2017/0105788 A1 | 4/2017 | Boudreaux |
| 2018/0161062 A1* | 6/2018 | Kaga ................. A61B 18/1445 |

(56) References Cited

U.S. PATENT DOCUMENTS

FOREIGN PATENT DOCUMENTS

| CN | 101820825 A | 9/2010 |
|---|---|---|
| CN | 103561664 A | 2/2014 |
| CN | 104271051 A | 1/2015 |
| DE | 298 11 977 U1 | 10/1998 |
| EP | 1769765 A1 | 4/2007 |
| EP | 2 436 328 A1 | 4/2012 |
| EP | 2 589 347 A1 | 5/2013 |
| JP | 2005-176905 A | 7/2005 |
| JP | 2010-264258 A | 11/2010 |
| JP | 2014-226318 A | 12/2014 |
| WO | WO 02/080798 A1 | 10/2002 |
| WO | WO 2009/149799 A1 | 12/2009 |
| WO | WO 2013/154923 A2 | 10/2013 |
| WO | WO 2013/115036 A1 | 5/2015 |
| WO | WO 2015/107916 A1 | 7/2015 |
| WO | WO 2016/044277 A1 | 3/2016 |

OTHER PUBLICATIONS

U.S. Appl. No. 15/284,837.
U.S. Appl. No. 15/284,855.
Chinese Office Action dated May 27, 2020 for Application No. 201680061293.1, 14 pages.
Chinese Office Action, The First Office Action, and First Search, dated Jun. 2, 2020, for Application No. CN 201680061050.8, 18 pgs.
Chinese Office Action, The First Office Action, and First Search, dated Jun. 2, 2020, for Application No. CN 201680061406.8, 20 pgs.
European Examination Report dated Aug. 1, 2019 for Application No. EP 16798019.2, 5 pgs.
European Examination Report dated Aug. 2, 2019 for Application No. EP 16784766.4, 7 pgs.
European Search Report and Written Opinion dated Oct. 30, 2019 for Application No. EP 19185541.0, 14 pgs.
European Search Report and Written Opinion dated Nov. 4, 2019 for Application No. EP 19185531.1, 12 pgs.
European Search Report and Written Opinion, Under Rule 164(2)(b) EPC, dated Oct. 29, 2019 for Application No. EP 16784766.4, 11 pgs.
European Search Report, Partial, and Provisional Written Opinion dated Aug. 2, 2019 for Application No. EP 19185531.1, 13 pgs.
European Search Report, Partial, and Provisional Written Opinion dated Aug. 5, 2019 for Application No. EP 19185541.0, 12 pgs.
International Search Report and Written Opinion dated Feb. 6, 2017 for Application No. PCT/US2016/057288, 14 pgs.
International Search Report and Written Opinion dated Mar. 3, 2017 for Application No. PCT/US2016/057277, 18 pgs.
International Search Report and Written Opinion dated Mar. 30, 2017 for Application No. PCT/US2016/057280, 19 pgs.
Japanese Office Action, Notice of Reasons for Refusal, Search Report by Registered Search Organization, dated Oct. 6, 2020 for Application No. JP 2018-539244, 23 pgs.
Japanese Office Action, Notice of Reasons for Refusal, Search Report by Registered Search Organization, dated Oct. 6, 2020 for Application No. JP 2018-539245, 22 pgs.
Japanese Office Action, Notice of Reasons for Refusal, Search Report by Registered Search Organization, dated Oct. 6, 2020 for Application No. JP 2018-539246, 22 pgs.
U.S. Appl. No. 61/410,603, filed Nov. 5, 2010.
U.S. Appl. No. 62/243,189, filed Oct. 19, 2015.
U.S. Appl. No. 62/363,411, filed Jul. 18, 2016.

* cited by examiner

SURGICAL INSTRUMENT WITH DUAL MODE END EFFECTOR AND MODULAR CLAMP ARM ASSEMBLY

This application is a continuation of U.S. application Ser. No. 15/284,855, filed Oct. 4, 2016, published as U.S. Pub. No. 2017/0105788 on Apr. 20, 2017, and patented as U.S. Pat. No. 10,893,914 on Dec. 29, 2020, entitled "Surgical Instrument with Dual Mode End Effector and Modular Clamp Arm Assembly," the disclosure of which is incorporated by reference herein.

PRIORITY

This application claims priority to U.S. Provisional Patent App. No. 62/363,411, entitled "Surgical Instrument with Dual Mode End Effector," filed Jul. 18, 2016, the disclosure of which is incorporated by reference herein.

This application also claims priority to U.S. Provisional Patent App. No. 62/243,189, entitled "Surgical Instrument with Dual Mode End Effector," filed Oct. 19, 2015, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2020, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2020, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1A:
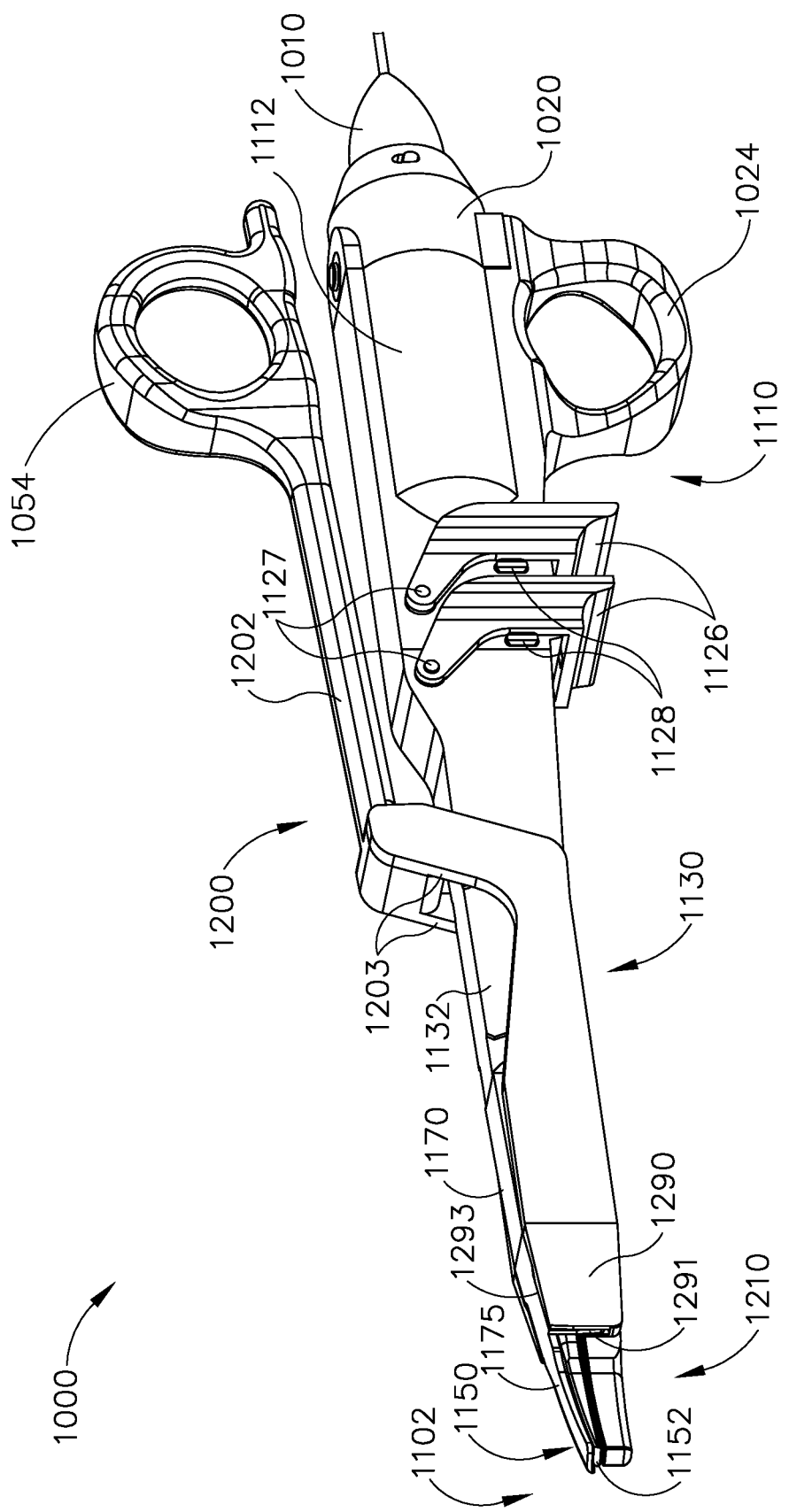
FIG. 1A depicts a perspective view of an exemplary surgical instrument, with an end effector in a closed configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument for Open Surgical Procedures

A. Overview

Figure 1B:
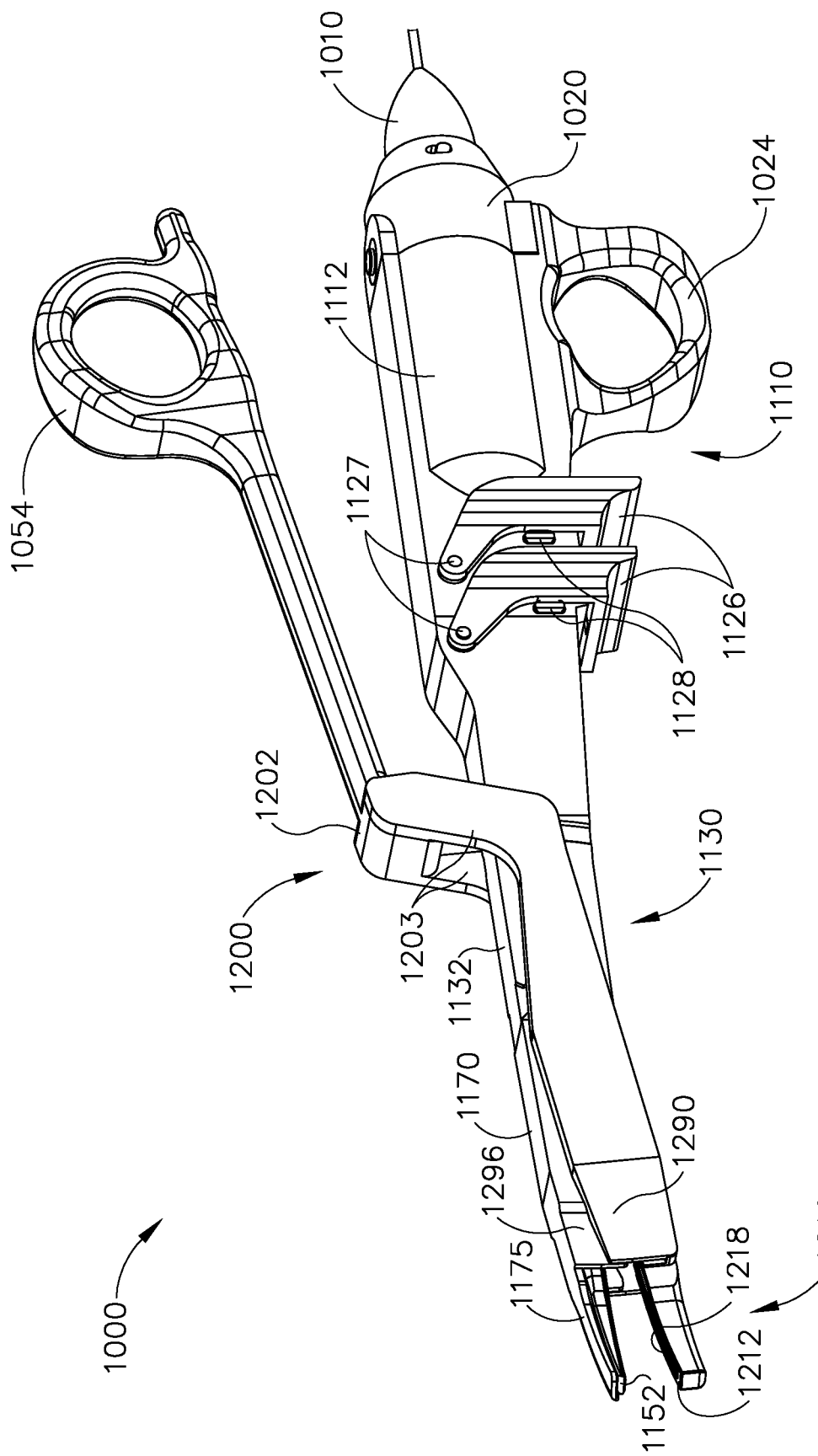
FIG. 1B depicts a perspective view of the instrument of FIG. 1A, with the end effector in an open configuration.

FIGS. 1A-1B show an exemplary ultrasonic surgical instrument (1000) with a clamp arm assembly that is detachable from a shaft assembly. Instrument (1000) is capable of delivering both ultrasonic energy and radio frequency (RF) energy to a surgical site. At least part of instrument (1000) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (1000) is operable to cut tissue and seal or weld tissue (e.g., a blood vessel, etc.) substantially simultaneously.

It should also be understood that instrument (1000) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (1000) may have various structural and functional similarities with the devices taught in any of the other references that are cited and incorporated by reference herein. Instrument (1000) of this example comprises a plug (1010), a proximal casing (1020), handle assembly (1110), a shaft assembly (1130), a blade assembly (1150), a clamp arm assembly (1200), and an end effector (1102). As will be described in greater detail below, clamp arm assembly (1200) may be selectively attached to handle assembly (1110) and detached from handle assembly (1110). The ability to selectively attach and detach clamp arm assembly (1200) from handle assembly (1110) may provide additional benefits of reusability for either handle assembly (1110) or clamp arm assembly (1200).

Handle assembly (1110) comprises a body (1112) including a finger grip ring (1024) and a pair of buttons (1126). Clamp arm assembly (1200) partially pivots toward and away from body (1112) of handle assembly (1110). Clamp arm assembly (1200) includes a body (1202) with a thumb grip ring (1054). Thumb grip ring (1054) and finger grip ring (1024) together provide a scissor grip type of configuration. It should be understood, however, that various other suitable configurations may be used, including but not limited to a pistol grip configuration.

Figure 2:
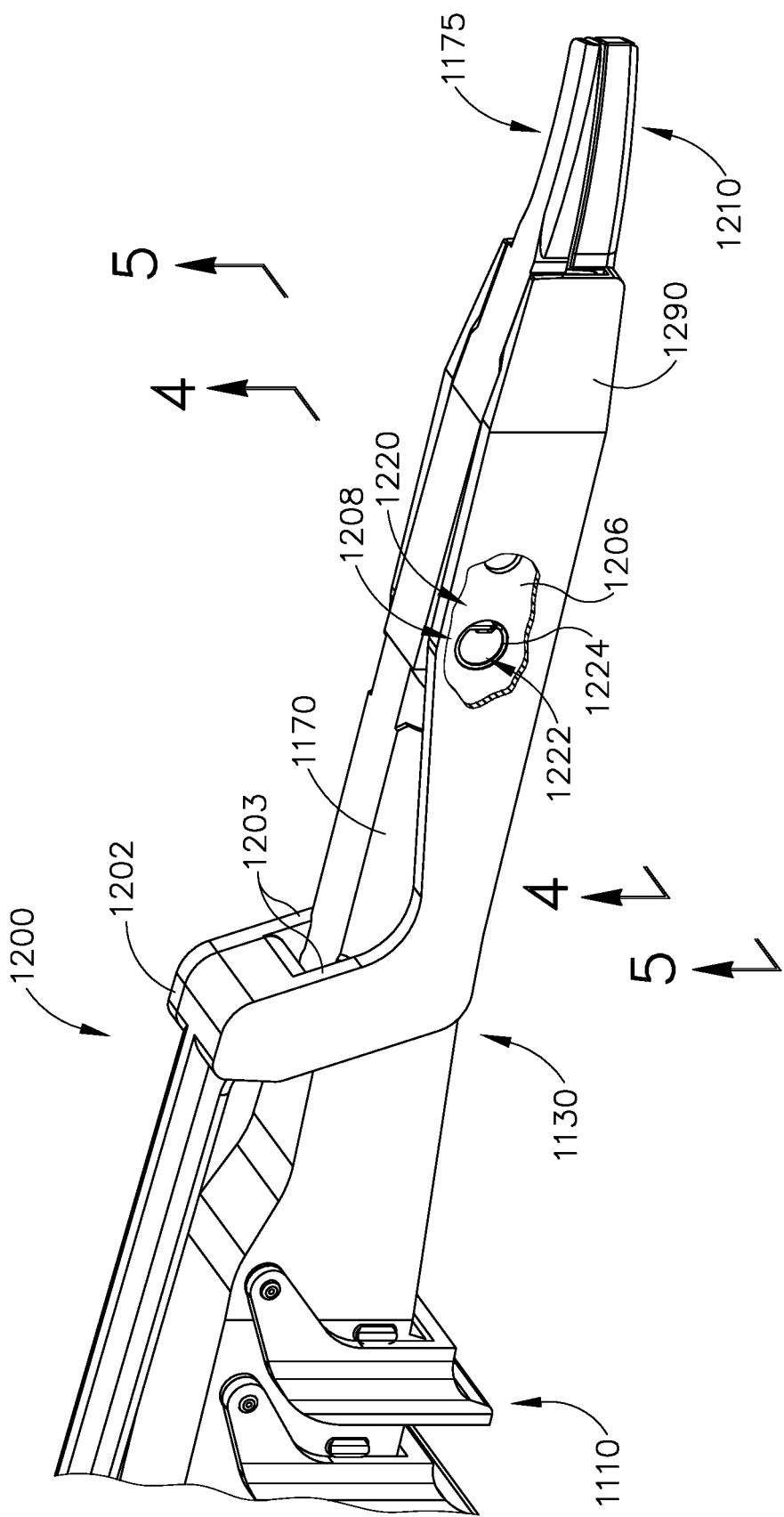
FIG. 2 depicts a partial perspective view of a distal portion of the instrument of FIG. 1A, with a portion of the clamp arm broken away to reveal a coupling assembly.

Shaft assembly (1130) comprises an outer sheath (1132) extending distally from body (1112). As will be described in greater detail below, outer sheath (1132) includes electrical traces and/or other electrically conductive features. As best seen in FIGS. 1A-2, end effector (1102) comprises an ultrasonic blade (1152) and a clamp pad assembly (1210). Ultrasonic blade (1152) extends distally from outer sheath (1132). Ultrasonic blade (1152) is a part of blade assembly (1150). Clamp arm assembly (1200) includes a pivotable member (1170) that is pivotally coupled to a Y-portion (1203) of body (1202) via a pair of bosses (1172) housed within a pair of complementary recess (1205) of Y-portion (1203).

Clamp pad assembly (1210) is an integral feature of body (1202) of clamp arm assembly (1200). More specifically, clamp pad assembly (1210) is fixed to Y-portion (1203) of body (1202). Therefore, clamp pad assembly (1210) may pivot relative to pivotable member (1170). Clamp pad assembly (1210) includes a clamp pad (1212) facing ultrasonic blade (1152) and an electrode (1218). As will be described in greater detail below, pivotable member (1170) is configured to receive blade assembly (1150) and a portion of shaft assembly (1130) via channel (1171). Clamp pad assembly (1210) is positioned distally in relation to complementary recess (1204); while body (1202) and thumb grip ring (1054) are positioned proximal to complementary recess (1202). Thus, as shown in FIGS. 1A-1B, clamp pad assembly (1210) is pivotable toward and away from both pivotable member (1170) and ultrasonic blade (1152) based on pivoting of thumb grip ring (1054) toward and away from body (1112) of handle assembly (1110). It should therefore be understood that an operator may squeeze thumb grip ring (1054) toward body (1112) to thereby clamp tissue between clamp pad assembly (1210) and ultrasonic blade (1152) to transect and/or seal the tissue using ultrasonic energy and/or RF energy. In some versions, one or more resilient members are used to bias clamp pad assembly (1210) to the open position shown in FIG. 1B. By way of example only, such a resilient member may comprise a leaf spring, a torsion spring, and/or any other suitable kind of resilient member.

An ultrasonic transducer assembly (not shown) is enclosed within proximal casing (1020) and body (1112) of handle assembly (1110). The transducer assembly may be coupled with a generator (not shown) via plug (1010). The transducer assembly may thereby electrical power from the generator and convert that power into ultrasonic vibrations through piezoelectric principles. The generator may include a power source and control module that is configured to provide a power profile to the transducer assembly that is particularly suited for the generation of ultrasonic vibrations through the transducer assembly. The generator may also be configured to provide a power profile that enables end effector (1102) to apply RF electrosurgical energy to tissue.

By way of example only, the generator may comprise a GEN 300 sold by Ethicon Endo-Surgery, Inc. of Cincinnati, Ohio. In addition, or in the alternative, the generator may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of the generator may be integrated into handle assembly (1110), and that handle assembly (1110) may even include a battery or other kind of on-board power source such that plug (1010) is omitted. Still other suitable forms that the generator may take, as well as various features and operabilities that the generator may provide, will be apparent to those of ordinary skill in the art in view of the teachings herein.

Ultrasonic vibrations that are generated by the transducer assembly are communicated along an acoustic waveguide (1154), which is disposed within a tube (1138). Waveguide (1154) is mechanically and acoustically coupled with the transducer assembly. Waveguide (1154) extends through shaft assembly (1130) to reach ultrasonic blade (1152). When ultrasonic blade (1052) is in an activated state (i.e., vibrating ultrasonically), ultrasonic blade (1052) is operable to effectively cut through and seal tissue, particularly when the tissue is being clamped between clamp pad (1212) and ultrasonic blade (1152). It should be understood that waveguide (1154) may be configured to amplify mechanical vibrations transmitted through waveguide (1154). Furthermore, waveguide (1154) may include features operable to control the gain of the longitudinal vibrations along waveguide (1154) and/or features to tune waveguide (1154) to the resonant frequency of the system.

In the present example, the distal end of ultrasonic blade (1152) is located at a position corresponding to an anti-node associated with resonant ultrasonic vibrations communicated through waveguide (1154), in order to tune the acoustic assembly to a preferred resonant frequency $f_o$ when the acoustic assembly is not loaded by tissue. When the transducer assembly is energized, the distal end of ultrasonic blade (1152) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly of the present example is activated, these mechanical oscillations are transmitted through the waveguide to reach ultrasonic blade (1152), thereby providing oscillation of ultrasonic blade (1152) at the resonant ultrasonic frequency. Thus, when tissue is secured between ultrasonic blade (1152) and clamp pad (1212), the ultrasonic oscillation of ultrasonic blade (1152) may simultaneously sever the tissue and denature the proteins in adjacent tissue cells, thereby providing a coagulative effect with relatively little thermal spread. In some versions, an electrical current may also be provided through ultrasonic blade (1152) and/or clamp pad (1212) to also seal the tissue.

As will be described in greater detail below, instrument (1000) is also configured to provide radiofrequency (RF) energy to a surgical site via end effector (1102). By way of example only, an operator may rely mainly on the use of ultrasonic energy from blade (1152) to sever tissue that is captured between ultrasonic blade (1152) and clamp pad (1212). The operator may further rely on the use of RF energy from end effector (1102) to seal the severed tissue. Of course, it will be understood that the ultrasonic energy from blade (1152) may seal tissue to some degree, such that the RF energy from end effector (1102) may supplement the sealing that would already be provided from the ultrasonic energy. It will also be understood that there may be instances where the operator may wish to simply wish to use end effector (1102) to only apply RF energy to tissue, without also applying ultrasonic energy to tissue. As will be appreciated from the description herein, some versions of instrument (1000) are capable of providing all of the above noted kinds of functionality.

An operator may activate buttons (1126) to selectively activate the transducer assembly to thereby activate ultrasonic blade (1152). In the present example, two buttons (1126) are provided. In some versions, one button (1126) is provided for activating ultrasonic blade (1152) at a first power profile (e.g., a first frequency and/or first amplitude) and another button (1126) is provided for activating ultrasonic blade (1152) at a second power profile (e.g., a second frequency and/or second amplitude). In some other versions, one button (1126) is provided for activating ultrasonic blade (1152) with ultrasonic energy, and the other button (1126) is provided for activating end effector (1102) with RF energy. It should be understood that any other suitable number of buttons and/or otherwise selectable power levels and/or power modalities may be provided. For instance, a foot pedal may be provided to selectively activate the transducer assembly.

Buttons (1126) of the present example are positioned such that an operator may readily fully operate instrument (1000) with a single hand. For instance, the operator may position their thumb in thumb grip ring (1054), position their ring finger in finger grip ring (1024), position their middle finger about body (1112), and manipulate buttons (1126) using their index finger. Of course, any other suitable techniques may be used to grip and operate instrument (1000); and buttons (1126) may be located at any other suitable positions.

The foregoing components and operabilities of instrument (1000) are merely illustrative. Instrument (1000) may be configured in numerous other ways as will be apparent to those of ordinary skill in the art in view of the teachings herein. By way of example only, at least part of instrument (1000) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. Pub. No. 2015/0080925, entitled "Alignment Features for Ultrasonic Surgical Instrument," published Mar. 19, 2015, now abandoned, the disclosure of which is incorporated by reference herein. . . . Additional merely illustrative features and variations for instrument (1000) will be described in greater detail below. It should be understood that the below described variations may be readily incorporated into to instrument (1000) described above and into any of the instruments described in any of the references that are cited herein, among others.

B. Exemplary Electrical Coupling Assembly

Figure 3:
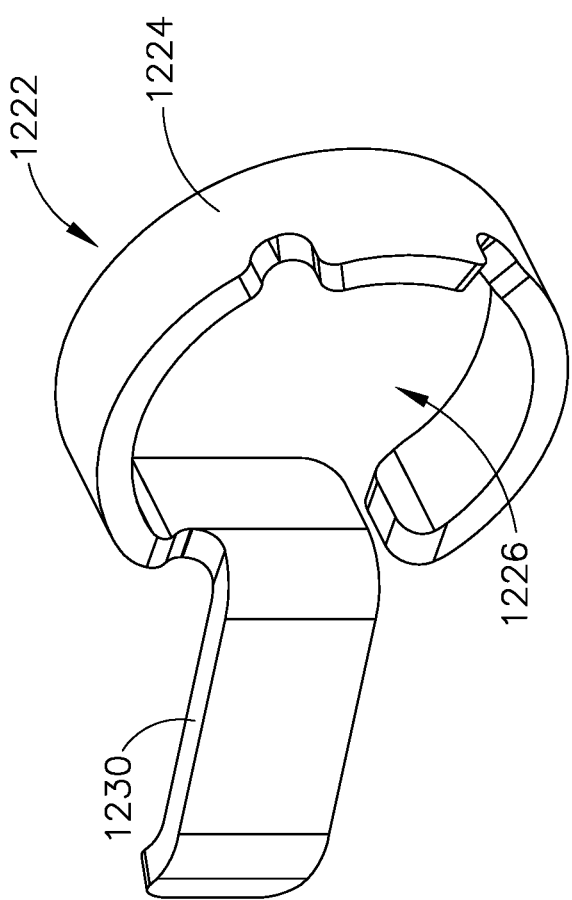
FIG. 3 depicts a perspective view of an exemplary conducting member of the coupling assembly of FIG. 2.
Figure 4:
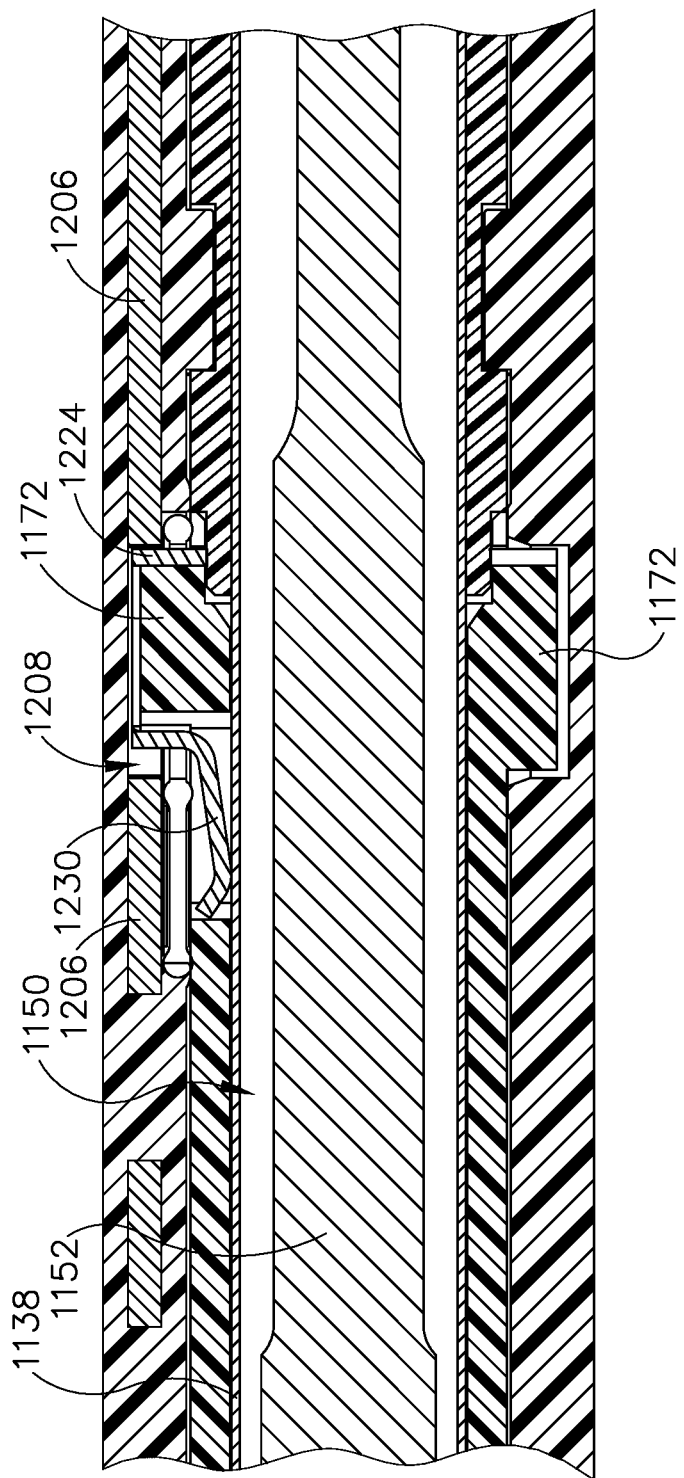
FIG. 4 depicts a cross-sectional view of the instrument of FIG. 1A, taken along line 4-4 of FIG. 2.

FIGS. 2-4 show an exemplary electrical coupling assembly (1220) that may be readily incorporated into instrument (1000). As can be seen in FIG. 2, electrical coupling assembly (1220) is incorporated into clamp arm assembly (1200) of instrument (1000) to provide electrical communication of RF energy between handle assembly (1110) and coupling assembly (1220).

Coupling assembly (1220) comprises a conducting member (1222) that is insertable into a coupling opening (1208) of inner core (1202) of clamp arm assembly (1200). As best seen in FIG. 3, conducting member (1222) comprises a receiving portion (1224) and a contact portion (1230). Conducting member (1222) generally comprises a material having both electrically conductive and resilient properties. In some examples, conducting member (1222) comprises an electrically conductive metal such as copper, gold, steel, aluminum, silver, etc. In still other examples, conducting member (1222) comprises an electrically conductive non-metallic material such as conducting polymers, silicides, graphite, etc.

Receiving portion (1224) of conducting member (1222) generally comprises a strip with a rectangular cross-section formed in a partial ring. Although receiving portion (1224) of the present example is shown as only defining a partial ring shape (e.g., breaking adjacent to contact portion (1230)), it should be understood that in other examples receiving portion (1224) forms a complete ring. The ring shape of receiving portion (1224) defines a central opening (1226). As will be described in greater detail below, opening (1226) is configured to receive boss (1172).

Receiving portion (1224) is configured to fit within coupling opening (1208) of inner core (1202). As will be described in greater detail below, receiving portion (1224) is generally held in position by the interface between inner core (1202) and boss (1172). In addition, or in alternative, receiving portion (1224) may be held in position by other suitable means. For instance, in some examples receiving portion (1224) is welded in position or otherwise fastened to inner core (1202). Regardless of how receiving portion (1224) is secured within coupling opening (1208), it should be understood that receiving portion (1224) is generally configured to provide a mechanical ground for contact portion (1230), as will be described in greater detail below.

Contact portion (1230) extends laterally and outwardly away from the outer diameter defined by receiving portion (1224). In particular, contact portion (1230) is shaped to form a resilient brush or contact. It should be understood that the term "resilient" used herein with respect to contact portion (1230) is used to refer to a rigid yet deformable character of contact portion (1230). For instance, contact portion (1230) is generally biased toward the position shown in FIG. 3. However, through engagement with various components of handle assembly (1110), contact portion (1230) may elastically deform in response to such engagement. After such engagement is removed, contact portion (1230) may return to its original configuration as shown in FIG. 3. As will be described in greater detail below, this shape permits contact portion (1230) to engage at least a portion of handle assembly (1110) to provide electrical communication between clamp arm assembly (1200) and handle assembly (1110).

As is best seen in FIG. 4, when conducting member (1222) is disposed within clamp arm assembly (1200) and clamp arm assembly (1200) is attached to handle assembly (1110) as described above, contact portion (1230) of conducting member (1222) extends transversely into handle assembly (1110). Inside handle assembly (1110), contact portion (1230) engages outer sheath (1132) of shaft assembly (1130). When contact portion (1230) is engaged with outer sheath (1132), contact portion (1230) deforms against outer sheath (1132) to provide electrical continuity between contact portion (1230) and outer sheath (1132). When in use, conducting member (1222) may rotate relative to boss (1172) as clamp arm assembly (1200) is pivoted. Because of the deformation and resilient character of contact portion (1230), it should be understood that even if conducting member (1222) engages in some rotation, contact portion (1230) will continue to bear against outer sheath (1132), thereby maintaining electrical continuity between contact portion (1230) and outer sheath (1132).

As described above, receiving portion (1224) is disposed within coupling opening (1208) of inner core (1202). Receiving portion (1224) is held in position between inner core (1202) and boss (1172). This generally secures receiving portion (1224) relative to inner core (1202) but may still permit some relative rotation between boss (1172) or inner core (1202). Receiving portion (1224) is generally secured to inner core (1204) to provide a mechanical ground such that receiving portion (1224) remains fixed while contact portion (1230) resiliently bears against outer sheath (1132). Additionally, receiving portion (1224) is in physical contact with inner core (1202). Because both inner core (1224) and receiving portion (1224) comprise electrical conductors, it should be understood that such physical contact between receiving portion (1224) and inner core (1204) provides electrical continuity between inner core (1204) and conducting member (1222).

Figure 5:
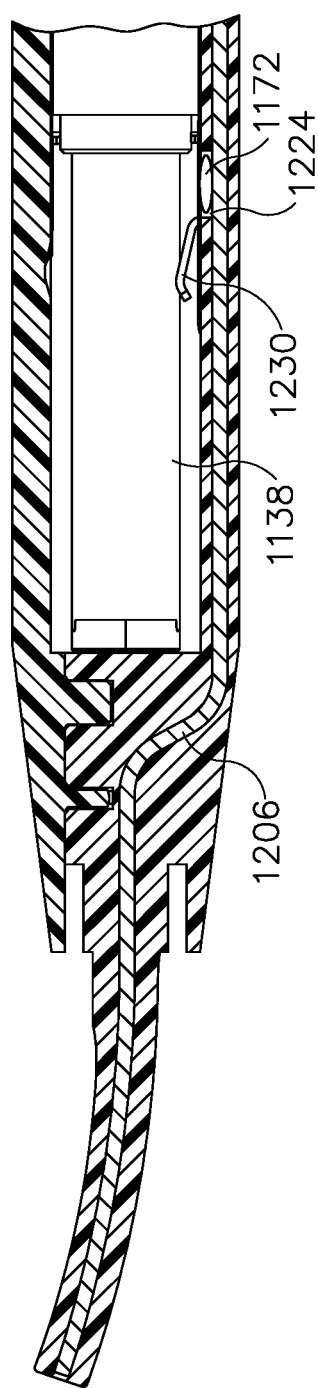
FIG. 5 depicts a cross-sectional view of the instrument of FIG. 1A, taken along line 5-5 of FIG. 2.

FIG. 5 shows an exemplary current path for coupling assembly (1220). As can be seen, structural core (1204) of body (1202) extends through body (1202) to the distal end of body (1202). Although not shown, it should be understood that at the distal end of body (1202) structural core (1204) is coupled to electrode (1218) as described above. Thus, structural core (1204) is configured to be in electrical communication with electrode (1218).

As described above, conducting member (1222) of coupling assembly (1220) is secured to body (1202) to be in electrical communication with structural core (1204). Thus, conducting member (1222) is configured to be in electrical communication with electrode (1218) via structural core (1204). As also described above, outer sheath (1132) of shaft assembly (1130) is also in electrical communication with conducting member (1222) via contact portion (1230). Thus, the engagement between contact portion (1230) and outer sheath (1132) also provides an electrical coupling between clamp arm assembly (1200) and handle assembly (1110). Because conducting member (1222) is configured to be in electrical communication with electrode (1218), the electrical coupling between outer sheath (1132) and contact portion (1230) is configured to permit electrical communication between handle assembly (1110) and electrode (1218). Outer sheath (1132) of handle assembly (1110) is then in electrical communication with generator (5). Thus, coupling assembly (1220) provides a current path from generator (5) to electrode so that an RF energy circuit may be formed with blade (152) and electrode (1218) when end effector (1102) is used to grasp tissue.

C. Exemplary Assembly

Figure 6A:
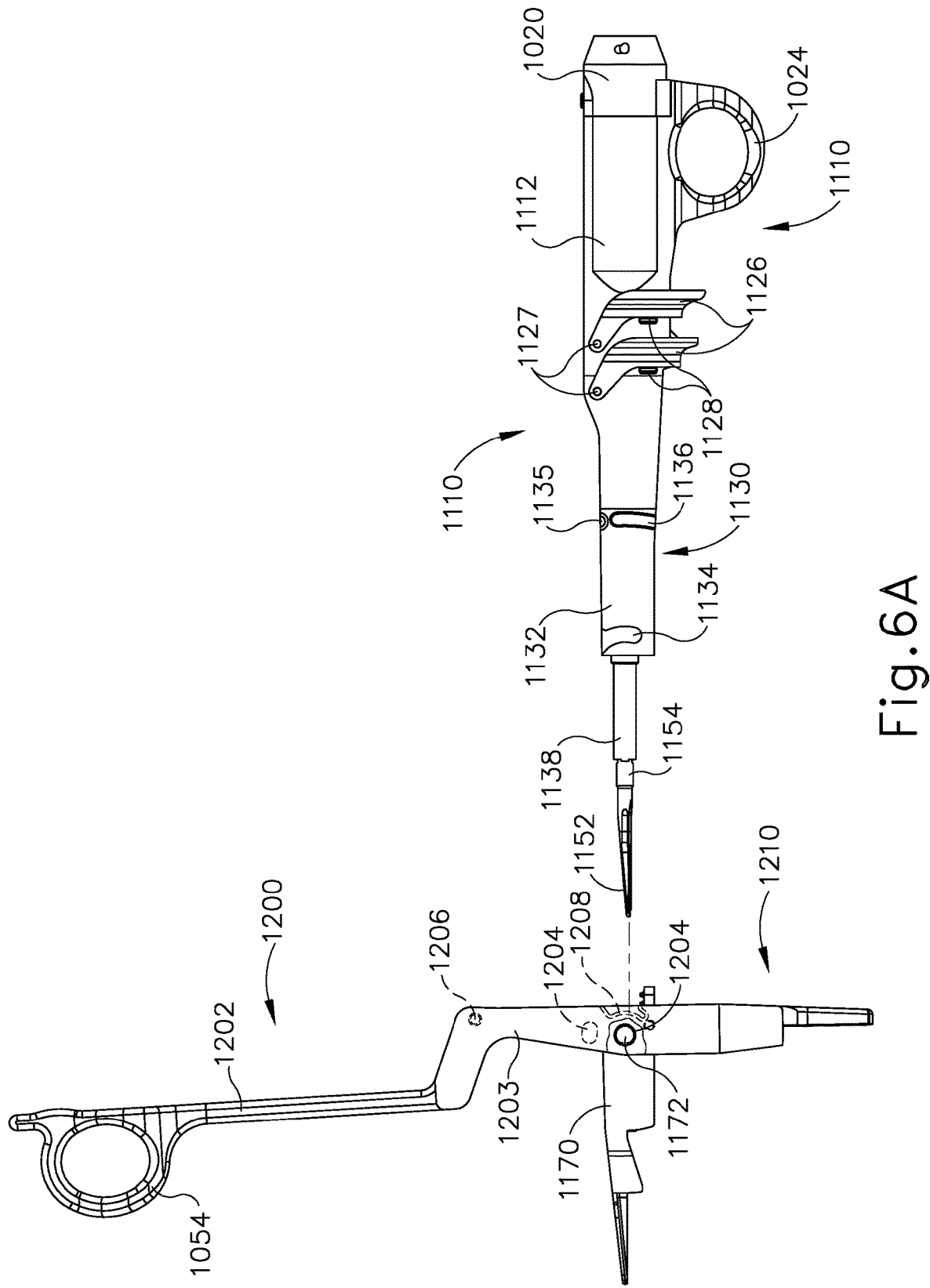
FIG. 6A depicts a side elevational view of the instrument of FIG. 1A, with a clamp arm assembly separated from a handle assembly.
Figure 6B:
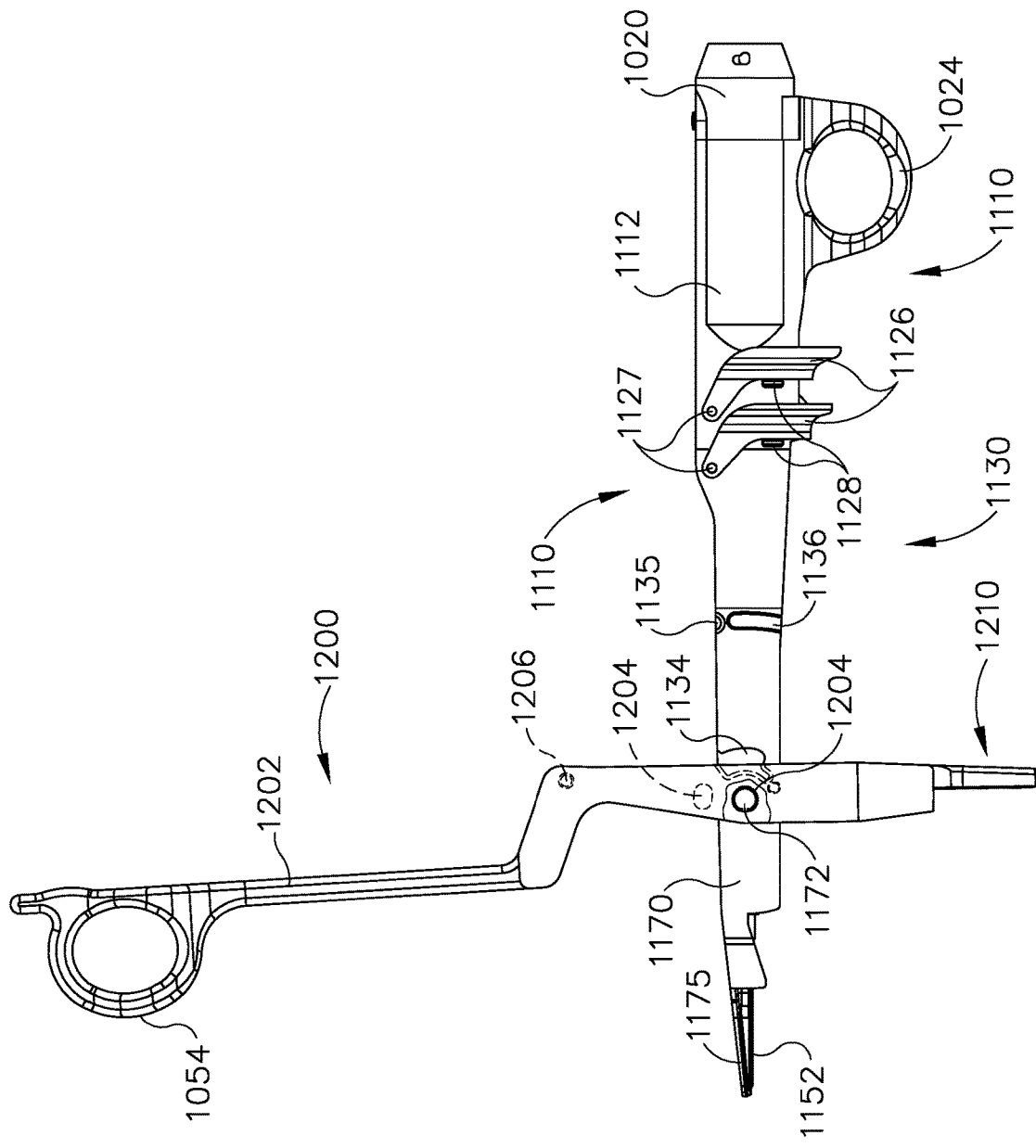
FIG. 6B depicts a side elevational view of the instrument of FIG. 1A, with the clamp arm assembly coupled with handle assembly, and with a clamp arm of the clamp arm assembly in a first pivotal position in relation to the handle assembly.
Figure 6C:
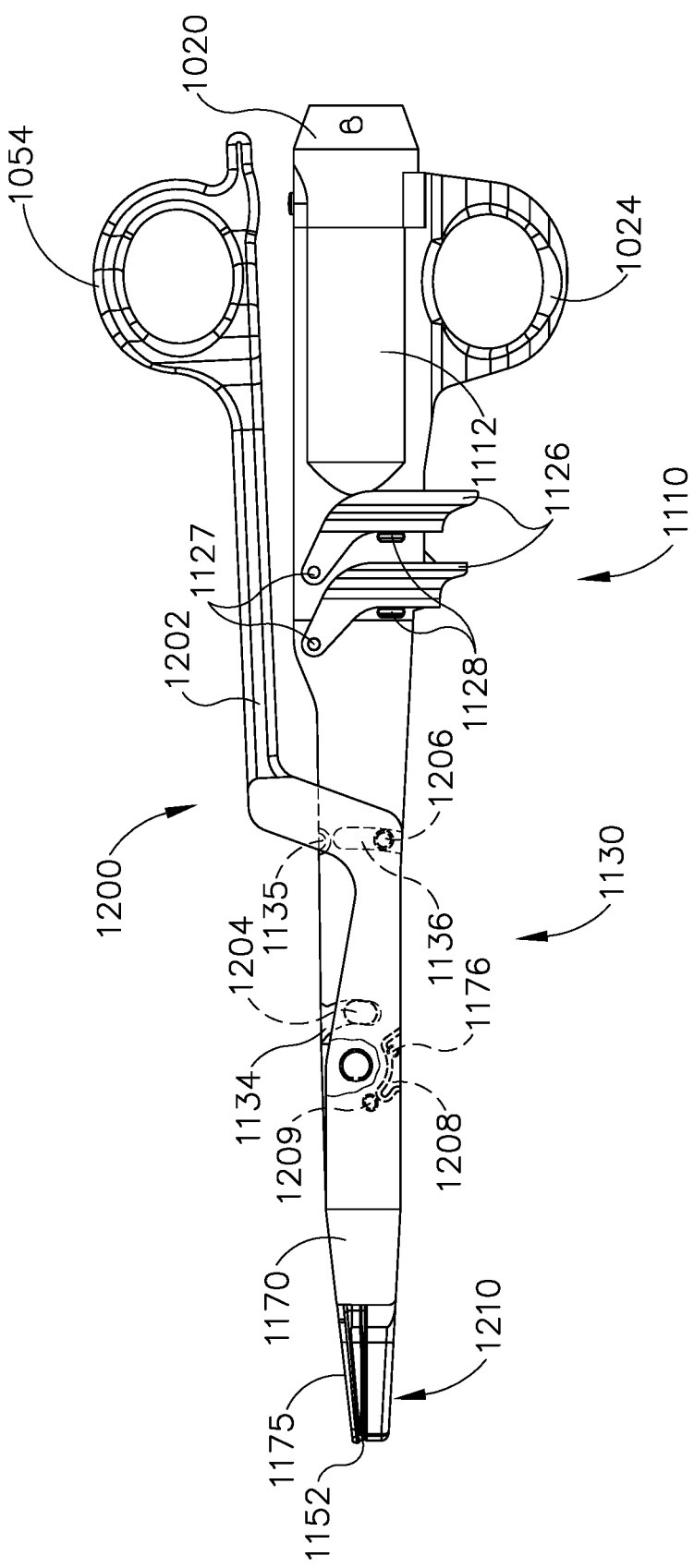
FIG. 6C depicts a side elevational view of the instrument of FIG. 1A, with the clamp arm assembly coupled with handle assembly, and with the clamp arm in a second pivotal position in relation to the handle assembly.

It may be beneficial to have a clamp arm assembly (1200) that may selectively detach from the rest of instrument (1000) so that certain aspects of instrument (1000) may be reusable while other features of instrument (1000) are disposed of. In such case, the reusable aspects of instrument (1000) will have to be cleaned and sterilized. Providing easy access to areas of instrument (1000) that need to be cleaned and sterilized may ensure a thorough cleaning for the next surgical procedure. To that end, clamp arm assembly (1200) may be selectively attached to handle assembly (1110) and detached from handle assembly (1110). FIGS. 6A-6C show clamp arm assembly (1200) coupling with handle assembly (1110). Clamp arm assembly (1200) of the present example couples with handle assembly (1110) by moving along a path that is aligned with the longitudinal axis of handle assembly (1100).

FIG. 6A shows clamp arm assembly (1200) decoupled from handle assembly (1110). At this point, pivotable member (1170) is pivoted to be substantially perpendicular with body (1202). Pivotable member (1170) includes detents (1176) that are positioned to rest within recesses (1209) located on the inner surface of Y-portion (1203) when pivotable member (1170) is substantially perpendicular with body (1202). Detents (1176) and recesses (1209) provide a snap fit relationship with each other. Therefore, when detents (1176) are within recesses (1209), detents (1176) and recesses (1209) interact to provide a frictional braking force. This fictional breaking force may help prevent pivotable member (1170) from rotating relative to body (1202); thereby assisting pivotable member (1170) in retaining a perpendicular relationship with body (1202). Detents (1176) are dimensioned such that without recesses (1209), detents would have an interference fit with the inside surfaces of Y-portion (1203). Maintaining a perpendicular relationship between pivotable member (1170) and body (1202) may allow for easier insertion of handle assembly (1110) into channel (1171) of pivotable member (1170). The frictional braking force provided by detents (1176) positioned in recesses (1209) may be overcome by hand. Therefore, once handle assembly is positioned within channel (1171), an operator may rotate body (1202) toward handle assembly (1110) to force detents (1176) to snap out of recesses (1209).

The inner surface of Y-portion (1203) includes another pair of arcuate recesses (1208) dimensioned to receive detents (1176). As mentioned above, detents (1176) are dimensioned to have an interference with the inside surfaces of Y-portion (1203). Recesses (1208) are dimensioned to allow detents (1176) to travel within recesses (1208) while body (1202) rotate towards and away from handle assembly (1110), without providing any frictional braking force due to the interference fit between inside surfaces of Y-portion (1203) and detents (1176). This relationship between recesses (1208) and detents (1176) may allow the operator to possess greater rotational control between clamp arm assembly (1200) and handle assembly (1110), as shown in FIG. 6C.

Y-portion (1203) of handle assembly (1200) also includes a pair of protrusions (1204) positioned along Y-portion (1203) to enter arcuate channels (1134) of shaft assembly (1130) when handle assembly (1200) rotates towards shaft assembly (1130). As shown in FIG. 6C, once protrusions (1204) enter channels (1134), shaft assembly (1130) and clamp arm assembly (1200) may no longer translate relative to each other. In other words, the protrusions (1204) and channels (1134) interact with each other to act as a longitudinal locking mechanism for instrument (1000). Additionally, channels (1134) define a path of angular rotation in which clamp arm assembly (1200) may rotate relative to handle assembly (1110). In the case at hand, as shown in FIG. 6C, channels (1134) are long enough to allow clamp pad assembly (1210) to close against blade (1152).

Y-portion (1203) also includes an additional pair of detents (1206) that are positioned to mate with indicating recesses (1135) and arcuate angle channels (1136). Detents (1206) are designed to slide within angle channel (1136) while clamp pad assembly (1201) rotates relative to blade (1152) at a predetermined range of angles. When clamp arm assembly (1200) rotates toward handle assembly (1110), detents (1206) provide tactile feedback when transitioning from indicating recesses (1135) to angle channels (1136). This tactile feedback indicates to the operator that clamp arm assembly (1200) is how sufficiently coupled to handle shaft assembly (1130) and ready for use.

During operation, clamp pad assembly (1210) may rotate to an angle where detents (1206) snap out of angle channels (1136) and into indicating recesses (1135). This may provide tactile feedback to an operator indicating that clamp pad assembly (1210) has rotated past the predetermined rage of operating angles defined by angle channels (1136). This feedback may indicate to the operator user that clamp pad assembly (1201) is at an angle relative to blade (1152) beyond the predetermined range of operating angles.

II. Exemplary Instrument with Clamp Arm Having Compound Lever Assembly

A. Overview

Figure 7A:
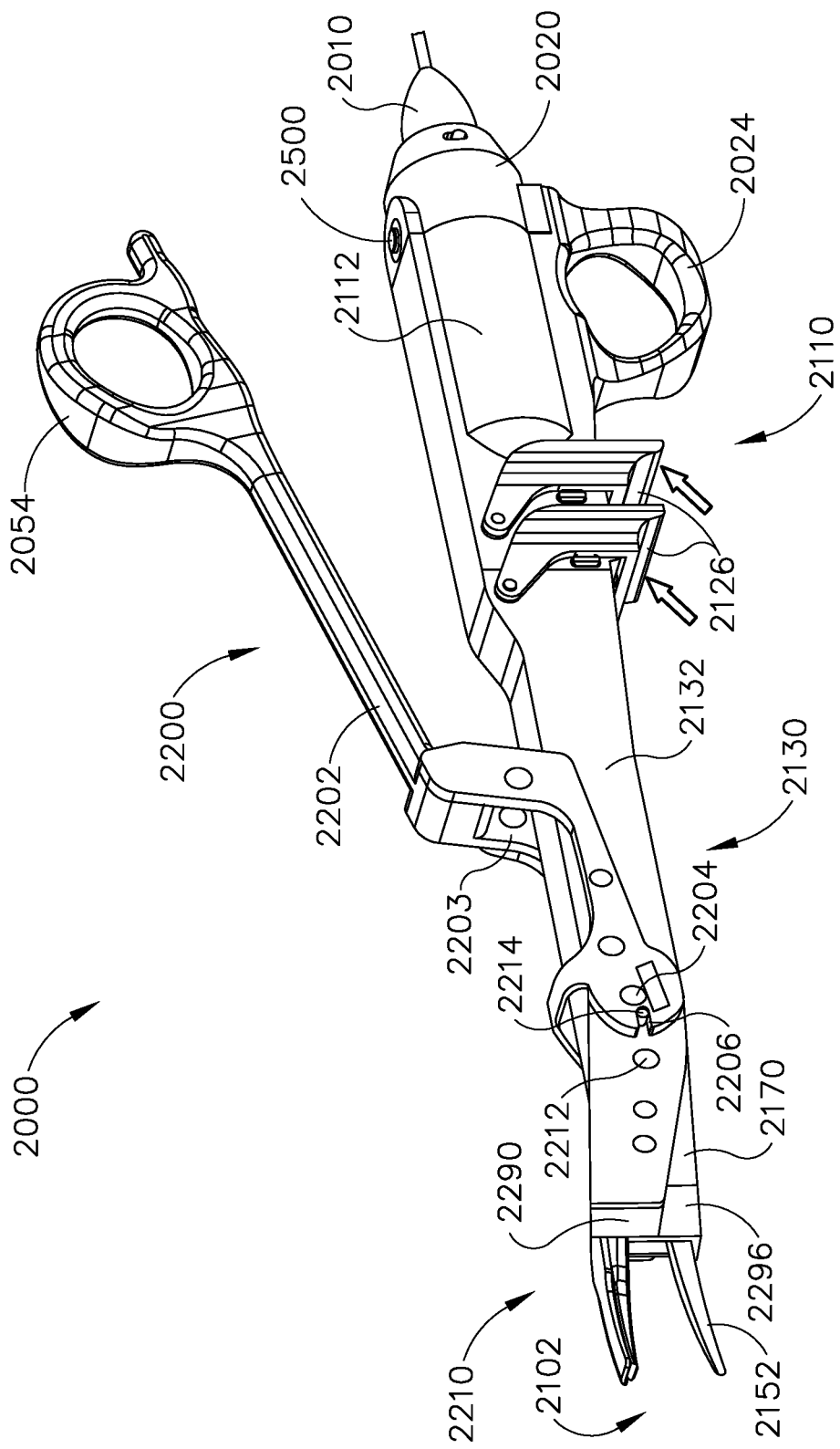
FIG. 7A depicts a perspective view of another exemplary surgical instrument, with an end effector of the instrument in an open configuration.
Figure 7B:
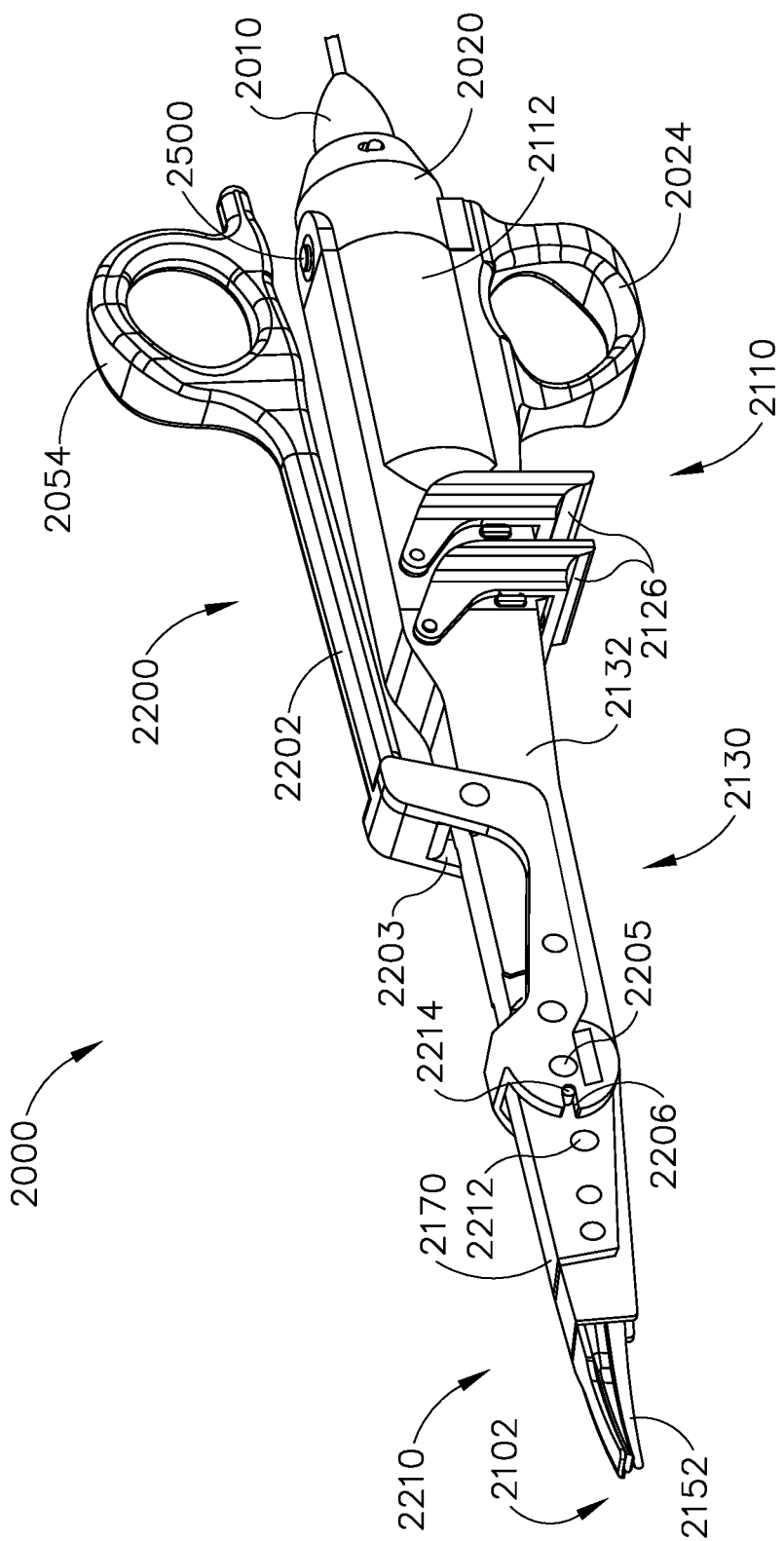
FIG. 7B depicts a perspective view of the instrument of FIG. 7A, with the end effector in a closed configuration.

In the example of instrument (1000) provided above, clamp pad assembly (1210) is on the opposite side of ultrasonic blade (1152) as body (1202) and thumb grip ring (1054) of clamp arm assembly (1200). However, in some instances, it may be desirable to have clamp pad assembly (1210) on the same side of ultrasonic blade (1152) as body (1202) and thumb grip ring (1054) of clamp arm assembly (1200). For instance, when dissecting the liver, it may be desirable to press ultrasonic blade (1152), while activated, into the liver and then rotate clamp pad assembly (1210) toward ultrasonic blade (1152) to dissect the liver parenchyma. Having ultrasonic blade (1152) below clamp pad assembly (1210) may give an operator better control and visualization of an instrument to perform the desired task. FIGS. 7A-7B show an exemplary alternative instrument (2000) that provides a clamp pad assembly that is on the same side of an ultrasonic blade as a body and thumb grip ring of a clamp arm assembly.

In particular, FIGS. 7A-7B show instrument (2000) having a removable clamp arm assembly (2200), with a clamp pad assembly (2210) being located above ultrasonic blade (2152) and on the same side of instrument (2000) as thumb grip ring (2054). Instrument (2000) has an assembly similar to instrument (1000) except for the differences discussed below. It should be understood that instrument (2000) may be capable of delivering both ultrasonic energy and radio frequency (RF) energy to tissue at a surgical site in accordance with the teachings herein.

Instrument (2000) of this example comprises a plug (2010), a proximal casing (2020), handle assembly (2110), a shaft assembly (2130), an ultrasonic blade (2152) extending distally from shaft assembly (2130), a clamp arm assembly (2200), and an end effector (2102). As will be described in greater detail below, clamp arm assembly (2200) may be selectively attached to shaft assembly (2130) and detached from shaft assembly (2130). The ability to selectively attach and detach clamp arm assembly (2200) from shaft assembly (2130) may provide additional benefits of reusability for either handle assembly (2110) or clamp arm assembly (2200).

Handle assembly (2110) and shaft assembly (2130) are substantially the same as handle assembly (1110) and shaft assembly (1130) described above. For instance, handle assembly (2110) comprises a body (2112) including a finger grip ring (2024) and a pair of buttons (2126). Shaft assembly (2130) comprises an outer sheath (2132) extending distally from body (2112). It should therefore be understood that the primary differences between instrument (2000) and instrument (1000) are related to clamp arm assembly (2200).

Clamp arm assembly (2200) partially pivots toward and away from body (2112) of handle assembly (2110). Clamp arm assembly (2200) includes a body (2202) with a thumb grip ring (2054) and a Y-portion (2203). Thumb grip ring (2054) and finger grip ring (2024) together provide a scissor grip type of configuration. It should be understood, however, that various other suitable configurations may be used, including but not limited to a pistol grip configuration.

Figure 8A:
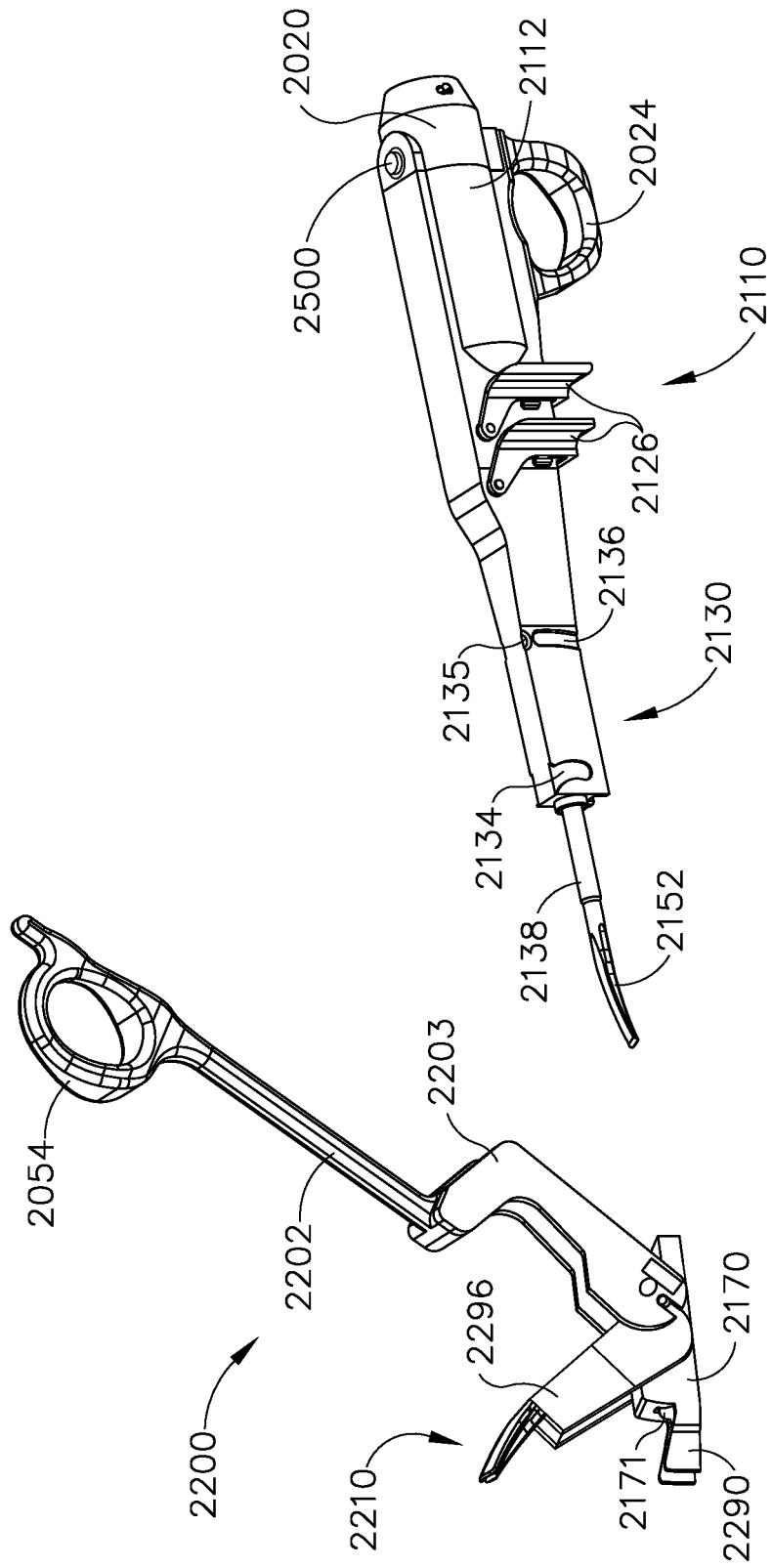
FIG. 8A depicts a perspective view of the instrument of FIG. 7A, with a clamp arm assembly separated from the handle assembly.
Figure 8B:
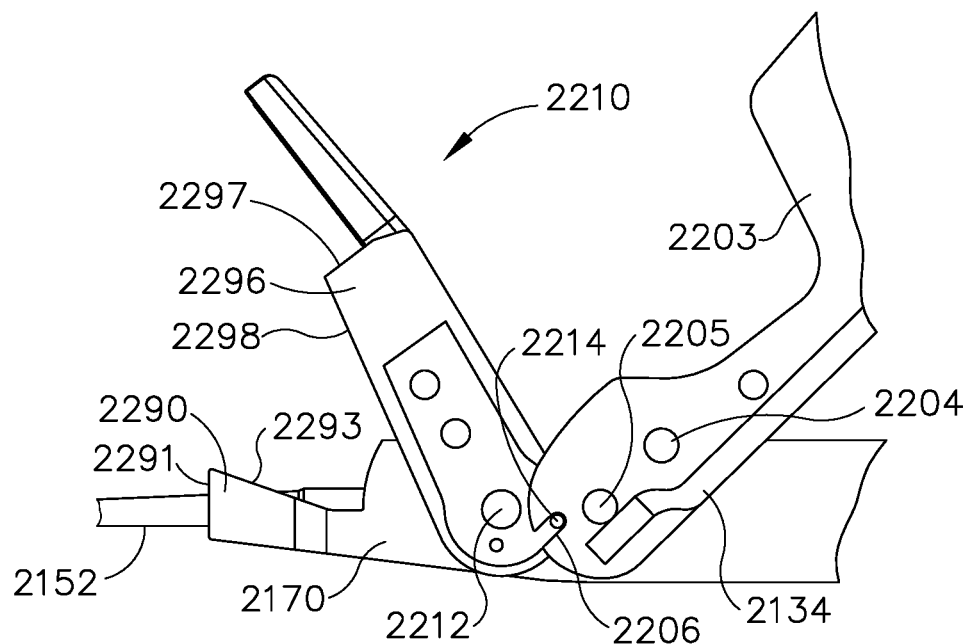
FIG. 8B depicts an enlarged side elevational view of a distal portion of the instrument of FIG. 7A, with the clamp arm assembly coupled with the handle assembly, and with the clamp arm assembly in a first pivotal state.

As best seen in FIGS. 8A-8B, end effector (2102) comprises an ultrasonic blade (2152) and a clamp pad assembly (2210). Ultrasonic blade (2152) extends distally from outer sheath (2132). Clamp arm assembly (2200) also comprises a receiving member (2170) and clamp pad assembly (2210). Receiving member (2170) defines a channel (2171) that is configured to receive ultrasonic blade (2152) and house tube (2138) of shaft assembly (2130). Y-portion (2203) is pivotally fixed to receiving member (2170) via pin (2205). Therefore, when receiving member (2170) houses tube (2138) of shaft assembly (2130), body (2202) of clamp arm assembly (2200) may rotate toward and away shaft assembly (2130) and housing assembly (2110).

Additionally, clamp pad assembly (2210) is pivotally fixed to receiving member (2170) via pin (2212). Clamp pad assembly (2210) is also connected to Y-portion (2203) between pins (2205, 2212) via a slot (2206) and pin (2214) connection. Clamp pad assembly (2210) and Y-portion (2203) thus form a compound lever assembly. Therefore, when body (2202) of clamp arm assembly (2200) rotates toward and away shaft assembly (2130) and housing assembly (2110) via pin (2205), slot (2206) and pin (2214) connection simultaneously rotate clamp pad assembly (2210) via pin (2212) in the opposite angular direction. For example, as seen in FIGS. 7A-7B, when thumb grip ring (2054) rotates body (2202) via pin (2204) toward handle assembly (2110), the distal end of clamp pad assembly (2210) rotates toward ultrasonic blade (2152). It should therefore be understood that an operator may squeeze thumb grip ring (2054) toward body (2112) to thereby clamp tissue between clamp pad assembly (2210) and ultrasonic blade (2152) to transect and/or seal the tissue. In some versions, one or more resilient members are used to bias clamp pad assembly (2210) to the open position shown in FIG. 7A. By way of example only, such a resilient member may comprise a leaf spring, a torsion spring, and/or any other suitable kind of resilient member.

An ultrasonic transducer assembly (not shown) is enclosed within proximal casing (2020) and body (2112) of handle assembly (2110). The transducer assembly may be coupled with a generator (not shown) via plug (2010). The transducer assembly may thereby electrical power from the generator and convert that power into ultrasonic vibrations through piezoelectric principles. The generator may include a power source and control module that is configured to provide a power profile to the transducer assembly that is particularly suited for the generation of ultrasonic vibrations through the transducer assembly. The generator may also be configured to provide a power profile that enables end effector (2102) to apply RF electrosurgical energy to tissue.

By way of example only, the generator may comprise a GEN 300 sold by Ethicon Endo-Surgery, Inc. of Cincinnati, Ohio. In addition, or in the alternative, the generator may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of the generator may be integrated into handle assembly (2110), and that handle assembly (2110) may even include a battery or other kind of on-board power source such that plug (2010) is omitted. Still other suitable forms that the generator may take, as well as various features and operabilities that the generator may provide, will be apparent to those of ordinary skill in the art in view of the teachings herein.

Ultrasonic vibrations that are generated by the transducer assembly are communicated along an acoustic waveguide (2054), which is disposed within a tube (2138). Waveguide (2054) is mechanically and acoustically coupled with the transducer assembly. Waveguide (2054) extends through shaft assembly (2130) to reach ultrasonic blade (2152). When ultrasonic blade (2052) is in an activated state (i.e., vibrating ultrasonically), ultrasonic blade (2052) is operable to effectively cut through and seal tissue, particularly when the tissue is being clamped between clamp pad (2212) and ultrasonic blade (2152). It should be understood that waveguide (2054) may be configured to amplify mechanical vibrations transmitted through waveguide (2054). Furthermore, waveguide (2054) may include features operable to control the gain of the longitudinal vibrations along waveguide (2054) and/or features to tune waveguide (2054) to the resonant frequency of the system.

In the present example, the distal end of ultrasonic blade (2152) is located at a position corresponding to an anti-node associated with resonant ultrasonic vibrations communicated through waveguide (2054), in order to tune the acoustic assembly to a preferred resonant frequency $f_o$ when the acoustic assembly is not loaded by tissue. When the transducer assembly is energized, the distal end of ultrasonic blade (2152) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly of the present example is activated, these mechanical oscillations are transmitted through the waveguide to reach ultrasonic blade (2152), thereby providing oscillation of ultrasonic blade (2152) at the resonant ultrasonic frequency. Thus, when tissue is secured between ultrasonic blade (2152) and clamp pad (2212), the ultrasonic oscillation of ultrasonic blade (2152) may simultaneously sever the tissue and denature the proteins in adjacent tissue cells, thereby providing a coagulative effect with relatively little thermal spread. In some versions, an electrical current may also be provided through ultrasonic blade (2152) and/or clamp pad (2212) to also seal the tissue.

As will be described in greater detail below, instrument (2000) is also configured to provide radiofrequency (RF) energy to a surgical site via end effector (2102). By way of example only, an operator may rely mainly on the use of ultrasonic energy from blade (2152) to sever tissue that is captured between ultrasonic blade (2152) and clamp pad (2212). The operator may further rely on the use of RF energy from end effector (2102) to seal the severed tissue. Of course, it will be understood that the ultrasonic energy from blade (2152) may seal tissue to some degree, such that the RF energy from end effector (2102) may supplement the sealing that would already be provided from the ultrasonic energy. It will also be understood that there may be instances where the operator may wish to simply wish to use end effector (2102) to only apply RF energy to tissue, without also applying ultrasonic energy to tissue. As will be appreciated from the description herein, some versions of instrument (2000) are capable of providing all of the above noted kinds of functionality.

An operator may activate buttons (2126) to selectively activate the transducer assembly to thereby activate ultrasonic blade (2152). In the present example, two buttons (2126) are provided. In some versions, one button (2126) is provided for activating ultrasonic blade (2152) at a first power profile (e.g., a first frequency and/or first amplitude) and another button (2126) is provided for activating ultrasonic blade (2152) at a second power profile (e.g., a second frequency and/or second amplitude). In some other versions, one button (2126) is provided for activating ultrasonic blade (2152) with ultrasonic energy, and the other button (2126) is provided for activating end effector (2102) with RF energy. It should be understood that any other suitable number of buttons and/or otherwise selectable power levels and/or power modalities may be provided. For instance, a foot pedal may be provided to selectively activate the transducer assembly.

Buttons (2126) of the present example are positioned such that an operator may readily fully operate instrument (2000) with a single hand. For instance, the operator may position their thumb in thumb grip ring (2054), position their ring finger in finger grip ring (1024), position their middle finger about body (2112), and manipulate buttons (2126) using their index finger. Of course, any other suitable techniques may be used to grip and operate instrument (2000); and buttons (2126) may be located at any other suitable positions.

The foregoing components and operabilities of instrument (2000) are merely illustrative. Instrument (2000) may be configured in numerous other ways as will be apparent to those of ordinary skill in the art in view of the teachings herein. By way of example only, at least part of instrument (2000) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,058 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. Pub. No. 2015/0080925, entitled "Alignment Features for Ultrasonic Surgical Instrument," published Mar. 19, 2015, now abandoned, the disclosure of which is incorporated by reference herein. Additional merely illustrative features and variations for instrument (2000) will be described in greater detail below. It should be understood that the below described variations may be readily incorporated into to instrument (2000) described above and into any of the instruments described in any of the references that are cited herein, among others.

B. Exemplary Assembly

Figure 8C:
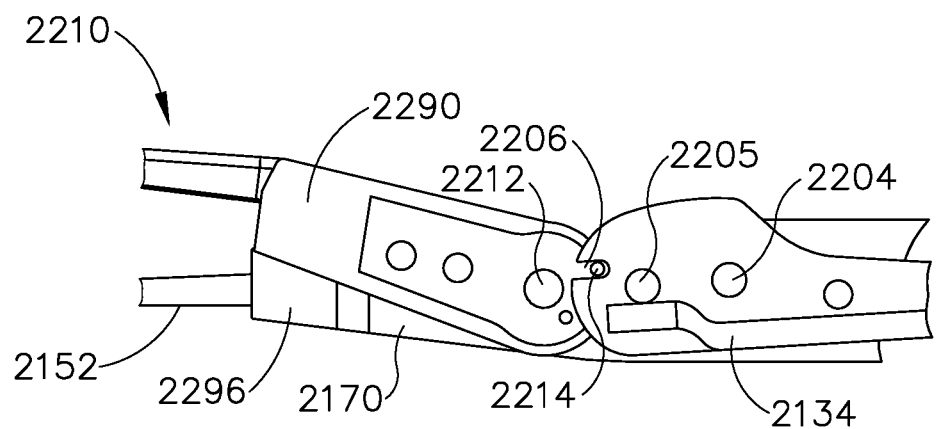
FIG. 8C depicts an enlarged side elevational view of a distal portion of the instrument of FIG. 7A, with the clamp arm assembly coupled with the handle assembly, and with the clamp arm assembly in a second pivotal state.

As mentioned above, clamp arm assembly (2200) may be attached and detached from handle assembly (2110). FIGS. 8A-8C show a process of coupling clamp arm assembly (2200) with handle assembly (2110). In particular, FIG. 8A shows clamp arm assembly (2200) decoupled from shaft assembly (2130) and handle assembly (2110). Y-portion (2203) of handle assembly (1200) includes a pair of protrusions (2204) that are configured to mate with shaft assembly (2130) after tube (2138) is housed within receiving member (2170). As shown in FIGS. 8B-8C, protrusions (2204) are positioned to enter actuate channels (2134) of shaft assembly (2130) when handle assembly (2200) rotates towards shaft assembly (2130). Once protrusions (2204) enter channels (2134), shaft assembly (2130) and clamp arm assembly (2200) may no longer translate relative to each other. In other words, protrusions (2204) and channels (2134) interact with each other to act as a locking mechanism for instrument (2000). Additionally, channels (2134) define a path of angular rotation in which clamp arm assembly (2200) may rotate relative to handle assembly (2110). In the case at hand, as shown in FIGS. 8B-8C, channels (2134) are long enough to allow clamp pad assembly (2210) to close against blade (2152).

C. Exemplary Tissue Stop

In some instances, end effector (2102) may have a proximal portion that is not capable of sufficiently severing and sealing tissue. In such instances, it may be beneficial to provide for a tissue stop that may prevent tissue from traveling to these proximal portions of an end effector. As seen in FIGS. 8A-8C, Y-portion (2203) comprises a first tissue stop (2290) while receiving member (2170) comprises a second tissue stop (2296). Like first tissue stop (1290) and second tissue stop (1296) described above, first tissue stop (2290) and second tissue stop (2296) rotate relative to each other. First tissue stop (2290) includes a first engagement surface (2291) and a top surface (2293). Second tissue stop (2296) includes a second engagement surface (2297) and a bottom surface (2298). If distal end of bottom surface (2298) overlaps with a portion of first tissue stop (2290) and distal end of top surface (2293) overlaps with a portion of second tissue stop (2296), first engagement surface (2291) and second engagement surface (2297) cooperate to prevent tissue from traveling to the proximal portion of end effector (2102) that is not capable of sufficiently severing and sealing tissue.

However, if distal end of bottom surface (2298) does not overlap with a portion of first tissue stop (2290) and/or distal end of top surface does not overlap with a portion of second tissue stop (2296), then tissue may be captured between bottom surface (2298) and top surface (2293) at a proximal portion of end effector (2102) that is not capable of sufficiently severing and sealing tissue. Y-portion (2203) may have detents (not shown) similar to detents (1206) discussed above. These detents may snap out of angle channels (2136) into indicating recesses (2135), providing tactile feedback, when the operator rotates clamp pad assembly to a position corresponding with first tissue stop (2290) and second tissue stop (2296) not overlapping. In other words, when detents (not shown) snap out of angle channels (2136) and into indicating recesses (2135), the tactile feedback may indicate to the operator that first tissue stop (2290) and second tissue stop (2296) are no longer overlapping. This may indicate to the operator that tissue may be captured between bottom surface (2298) and top surface (2293) at a proximal portion of end effector (2102) that is not capable of sufficiently severing and sealing tissue.

D. Exemplary Spot Coagulation and Symmetrical Blade

Figure 9:
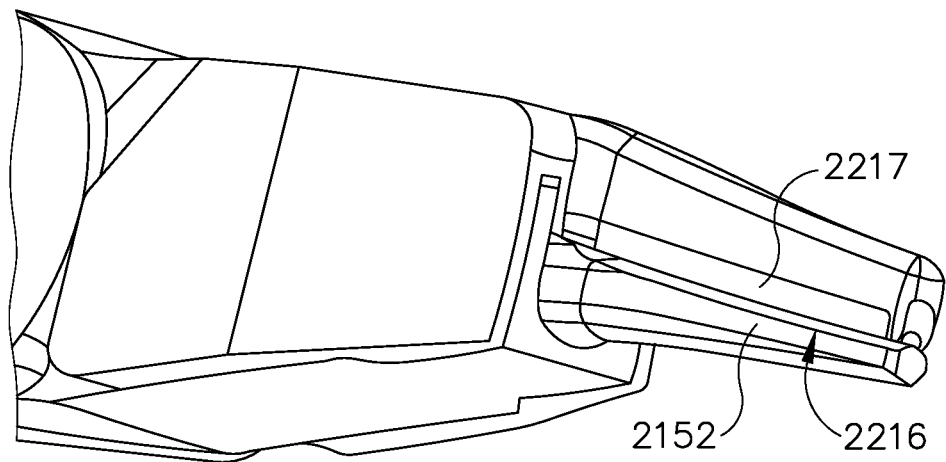
FIG. 9 depicts a perspective view of the end effector of FIG. 7A, with the end effector in a closed configuration.

In some instances, it may be desirable to provide for spot coagulation on targeted tissue without the use of clamping. In other words, the operator may wish to simply press one or more RF electrosurgical electrodes against tissue to provide spot coagulation of the tissue, without clamping the tissue between blade (2152) and clamp pad assembly (2210). As shown in FIG. 9, clamp pad assembly (2210) includes an electrode (2216) having an enlarged side lip (2217). Enlarged side lip (2217) laterally exposed when end effector (2102) is in a closed configuration. Enlarged side lip (2217) is configured to receive a spot coagulation pulse when clamp pad assembly (2210) is slightly opened in relation to ultrasonic blade (2152). A spot coagulation pulse may be activated when an operator presses button (2126) corresponding to a sealing function without having clamp arm assembly (2200) pressed against full clamp button (2500). In other words, when clamp arm assembly (2200) presses against full clamp button (2500), end effector (2102) is completely closed. When end effector (2102) is completely closed, pressing button (2126) activates sealing mode. When clamp arm assembly (2200) does not press against full clamp button (2500), end effector (2102) is at least partially open. When end effector (2102) is at least partially opened, pressing button (2126) corresponding to sealing mode activates a spot coagulation pulse.

III. Exemplary Modularity of Symmetric Ultrasonic Blade

As noted above, in some instances (e.g., liver dissection procedures, etc.), it may be desirable to have clamp pad assembly (2210) on the same side of ultrasonic blade (2152) as body (2202) and thumb grip ring (2054) of clamp arm assembly (2200). However, in some other instances (e.g., transection of a vessel, etc.), it may be desirable to have clamp pad assembly (1210) on the opposite side of ultrasonic blade (1152) as body (1202) and thumb grip ring (1054) of clamp arm assembly (1200). Moreover, it may be desirable to have both kinds of instrument configurations on hand for a given surgical procedure, with the option to choose between these two configurations depending on the particular task at hand during the surgical procedure. It may therefore be further desirable to provide a handle assembly that is capable of selectively receiving clamp arm assembly (1200) or clamp arm assembly (2200) in a modular fashion.

In the present example, handle assembly (2110) is capable of selectively receiving clamp arm assembly (1200) or clamp arm assembly (2200) in a modular fashion. Thus, when handle assembly (2110) is coupled with clamp arm assembly (1200), clamp pad assembly (1210) is on the opposite side of ultrasonic blade (2152) as body (1202) and thumb grip ring (1054) of clamp arm assembly (1200). By contrast, when handle assembly (2110) is coupled with clamp arm assembly (2200), clamp pad assembly (2210) is on the same side of ultrasonic blade (2152) as body (2202) and thumb grip ring (2054) of clamp arm assembly (2200).

Figure 10:
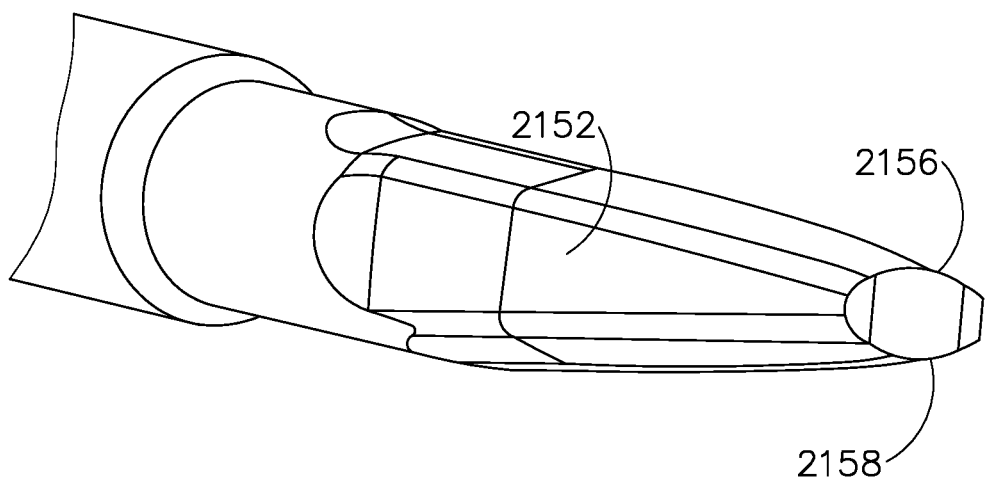
FIG. 10 depicts a perspective view of an ultrasonic blade of the end effector of FIG. 7A.

In order to provide compatibility with both clamp arm assemblies (1200, 2200), ultrasonic blade (2152) has symmetrical properties, as best seen in FIG. 10. Due to the symmetrical configuration of blade (2152) in this example, that a first side (2155) of blade (2152) may properly align with clamp pad assembly (2210) and a second side (2158) of blade (2152) may properly align with clamp pad assembly (1210). Therefore, handle assembly (2110) and shaft assembly (2130) may utilize either clamp arm assembly (1200, 2200), based on the operator's selection. In some instances, handle assembly (2110) with shaft assembly (2130) is provided in a kit with both clamp arm assemblies (1200, 2200), allowing the operator to readily choose which clamp arm assembly (1200, 2200) to use.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; and (d) a detent feature, wherein the detent feature is configured to provide tactile resistance to pivotal movement of the clamp arm relative to the body beyond a predefined pivot angle, wherein the detent feature is configured to permit pivotal movement of the clamp arm relative to the body beyond a predefined pivot angle upon application of a force sufficient to overcome the tactile resistance.

Example 2

The surgical instrument of Example 1, wherein the detent feature comprises a cantilevered member.

Example 3

A surgical instrument, comprising: (a) a body; (b) an ultrasonic blade extending distally from the body, wherein the ultrasonic blade is operable to apply ultrasonic energy to tissue; and (c) a clamp arm assembly pivotably coupled with the coupling post, wherein the clamp arm is operable to compress tissue against the ultrasonic blade, wherein the clamp arm assembly comprises (i) a clamp arm base, wherein the clamp arm base is configured to be secured to a distal end of the body, and (ii) a clamp arm pivotably coupled to the clamp arm base, wherein the clamp arm is operable to pivot toward the ultrasonic blade to thereby compress tissue against the ultrasonic blade while the clamp arm base is stationary relative to the body.

Example 4

The surgical instrument of Example 3, wherein the clamp arm assembly further comprises a detent assembly, wherein the detent assembly is configured to selectively maintain a first angular relationship between the clamp arm base and the clamp arm.

Example 5

The surgical instrument of Example 4, wherein the detent assembly is configured to selectively maintain a perpendicular relationship between the clamp arm base and the clamp arm when the clamp arm base is decoupled from the body.

Example 6

The surgical instrument of any one or more of Examples 3 through 5, wherein the clamp arm comprises a detent feature, wherein the body comprises a detent feature configured to complement the detent feature of the clamp arm, wherein the detent features of the clamp arm and the body are configured to selectively restrict pivotal movement of the clamp arm relative to the body when the clamp arm base is secured to the body.

Example 7

The surgical instrument of Example 39, wherein the detent feature of the body is positioned to be located proximal to the clamp arm base when the clamp arm base is secured to the body.

Example 8

A surgical instrument, comprising: (a) a body; (b) an ultrasonic blade extending distally from the body, wherein the ultrasonic blade is operable to apply ultrasonic energy to tissue; (c) a clamp arm, wherein the clamp arm is operable to compress tissue against the ultrasonic blade; and (d) a pivot assembly, wherein the clamp arm is pivotably coupled to the body at the pivot assembly, wherein the pivot assembly comprises: (i) a first link, wherein the first link is pivotably coupled with the body at a first pivot, (ii) a second link, wherein the clamp arm is secured to the second link, wherein the second link is distal to the first link, wherein the second link is pivotably coupled with the first link at a second pivot, wherein the second pivot is distal to the first pivot, wherein the second link is further pivotably coupled with the body at a third pivot, wherein the third pivot is distal to the second pivot.

Example 9

The surgical instrument of Example 8, wherein the first link has a distal portion and a proximal portion, wherein the first and second pivots are located at the distal portion, wherein the proximal portion includes a grip feature configured to be engaged by an operator to thereby drive the proximal portion toward the body.

Example 10

The surgical instrument of any one or more of Examples 8 through 9, wherein a proximal portion of the first link is pivotable toward and away from the body along a first path, wherein the clamp arm is pivotable toward and away from the body along a second path, wherein the body defines a longitudinal axis, wherein the first and second paths are on the same side of the longitudinal axis.

Example 11

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade, wherein the clamp arm comprises an electrode operable to apply RF energy to tissue, wherein a portion of the electrode is configured to be laterally exposed when the clamp arm is in a closed position in relation to the ultrasonic blade.

Example 12

A kit, comprising: (a) a first subassembly, wherein the first subassembly comprises: (i) a body, wherein the body defines a longitudinal axis, and (ii) an ultrasonic blade extending distally relative to the body; (b) a second subassembly, wherein the second subassembly is configured to removably couple with the first subassembly, wherein the second subassembly comprises: (i) a first clamp arm, wherein the first clamp arm is configured to be located on a first side of the longitudinal axis of the body when the second subassembly is coupled with the first subassembly, and (ii) a first clamp arm actuator, wherein the first clamp arm actuator is configured to be located on a second side of the longitudinal axis of the body when the second subassembly is coupled with the first subassembly, wherein the first clamp arm actuator is pivotable toward and away from the body to thereby pivot the first clamp arm toward and away from the ultrasonic blade when the second subassembly is coupled with the first subassembly; and (c) a third subassembly, wherein the third subassembly is configured to removably couple with the first subassembly, wherein the third subassembly comprises: (i) a second clamp arm, wherein the second clamp arm is configured to be located on the second side of the longitudinal axis of the body when the third subassembly is coupled with the first subassembly, and (ii) a second clamp arm actuator, wherein the second clamp arm actuator is configured to be located on the second side of the longitudinal axis of the body when the third subassembly is coupled with the first subassembly, wherein the second clamp arm actuator is pivotable toward and away from the body to thereby pivot the second clamp arm toward and away from the ultrasonic blade when the third subassembly is coupled with the first subassembly.

Example 13

The kit of Example 12, wherein the second subassembly further comprises a clamp arm base, wherein the clamp arm base is configured to be secured to a distal end of the body, wherein the first clamp arm is pivotably coupled to the clamp arm base.

Example 14

The kit of Example 13, wherein the second subassembly further comprises a detent assembly, wherein the detent assembly is configured to selectively maintain a first angular relationship between the clamp arm base and the first clamp arm.

Example 15

The kit of claim any one or more of Examples 12 through 14, wherein the third subassembly further comprises a pivot assembly, wherein the pivot assembly comprises: (i) a first link, wherein the first link is pivotably coupled with the body at a first pivot, and (ii) a second link, wherein the clamp arm is secured to the second link, wherein the second link is distal to the first link, wherein the second link is pivotably coupled with the first link at a second pivot, wherein the second pivot is distal to the first pivot, wherein the second link is further pivotably coupled with the body at a third pivot, wherein the third pivot is distal to the second pivot.

Example 16

The kit of Example 15, wherein the first link has a distal portion and a proximal portion, wherein the first and second pivots are located at the distal portion, wherein the proximal portion includes a grip feature configured to be engaged by an operator to thereby drive the proximal portion toward the body.

Example 17

The kit of any one or more of Examples 15 through 16, wherein a proximal portion of the first link is pivotable toward and away from the body along a first path, wherein the clamp arm is pivotable toward and away from the body along a second path, wherein the first and second paths are on the same side of the longitudinal axis.

Example 18

The kit of any one or more of Examples 12 through 17, wherein the second clamp arm comprises an electrode operable to apply RF energy to tissue.

Example 19

The kit of Example 19, wherein a portion of the electrode is configured to be laterally exposed when the clamp arm is in a closed position in relation to the ultrasonic blade.

Example 20

The kit of any one or more of Examples 12 through 19, wherein the ultrasonic blade has a first surface located on the first side of the longitudinal axis and a second surface located on a second side of the longitudinal axis, wherein the first and second surfaces have complementary profiles.

Example 21

The kit of Example 20, wherein the first surface is curved, wherein the second surface is curved.

Example 22

The kit of any one or more of Examples 12 through 21, wherein the second subassembly is configured to insertingly receive a distal portion of the body along the longitudinal axis.

Example 23

The kit of any one or more of Examples 12 through 22, wherein the third subassembly is configured to insertingly receive a distal portion of the body along the longitudinal axis.

Example 24

The kit of any one or more of Examples 12 through 23, wherein the ultrasonic blade extends along a first plane, wherein the longitudinal axis extends along the first plane, wherein the ultrasonic blade is symmetric about the first plane.

Example 25

The kit of one or more of Examples 12 through 24, wherein the first clamp arm comprises an electrode operable to apply RF energy to tissue.

Example 26

The kit of one or more of Examples 12 through 25, further comprising a transducer assembly, wherein the transducer assembly is operable to convert electrical power into ultrasonic vibrations.

Example 27

The kit of Example 26, wherein the body is configured to receive the transducer assembly.

Example 28

The kit of any one or more of Examples 12 through 27, wherein a conductive element of the first subassembly is configured to establish electrical continuity with a conductive element of the second subassembly upon coupling of the second subassembly with the first subassembly.

Example 29

A kit, comprising: (a) a first subassembly, wherein the first subassembly comprises: (i) a body, and (ii) an ultrasonic blade extending distally relative to the body; (b) a second subassembly, wherein the second subassembly is configured to removably couple with the first subassembly, wherein the second subassembly comprises: (i) a first clamp arm, wherein the first clamp arm is configured to be located on a first side of the ultrasonic blade when the second subassembly is coupled with the first subassembly, and (ii) a first clamp arm actuator, wherein the first clamp arm actuator is pivotable toward and away from the body to thereby pivot the first clamp arm toward and away from the ultrasonic blade when the second subassembly is coupled with the first subassembly; and (c) a third subassembly, wherein the third subassembly is configured to removably couple with the first subassembly, wherein the third subassembly comprises: (i) a second clamp arm, wherein the second clamp arm is configured to be located on a second side of the longitudinal axis of the body when the third subassembly is coupled with the first subassembly, and (ii) a second clamp arm actuator, wherein the second clamp arm actuator is pivotable toward and away from the body to thereby pivot the second clamp arm toward and away from the ultrasonic blade when the third subassembly is coupled with the first subassembly.

Example 30

The kit of Example 29, wherein the body defines a longitudinal axis, wherein the first clamp arm is configured to be located on a first side of the longitudinal axis when the second subassembly is coupled with the first subassembly, wherein the first clamp arm actuator is configured to be located on a second side of the longitudinal axis when the second subassembly is coupled with the first subassembly, wherein the second clamp arm is configured to be located on the second side of the longitudinal axis when the second subassembly is coupled with the first subassembly, wherein the second clamp arm actuator is configured to be located on the second side of the longitudinal axis when the second subassembly is coupled with the first subassembly.

Example 31

A kit, comprising: (a) a first subassembly, wherein the first subassembly comprises: (i) a body, and (ii) an ultrasonic blade extending distally relative to the body; (b) a second subassembly, wherein the second subassembly is configured to removably couple with the first subassembly, wherein the second subassembly comprises: (i) a first clamp arm, (ii) a first clamp arm actuator, and (iii) a single pivot, wherein the first clamp arm and the first clamp arm actuator are pivotable together toward and away from the body about the single pivot to thereby pivot the first clamp arm toward and away from the ultrasonic blade when the second subassembly is coupled with the first subassembly; and (c) a third subassembly, wherein the third subassembly is configured to removably couple with the first subassembly, wherein the third subassembly comprises: (i) a second clamp arm, (ii) a second clamp arm actuator, (iii) a first pivot, wherein the second clamp arm is pivotable about the first pivot to thereby pivot the second clamp arm toward and away from the ultrasonic blade when the third subassembly is coupled with the first subassembly, and (iv) a second pivot, wherein the second clamp arm actuator is pivotable about the second pivot to thereby drive the second clamp arm to pivot toward and away from the ultrasonic blade when the third subassembly is coupled with the first subassembly.

V. Miscellaneous

It should be understood that the various teachings herein may be readily combined with the various teachings of U.S. patent application Ser. No. 15/284,819, entitled "Surgical Instrument with Dual Mode End Effector and Side-Loaded Clamp Arm Assembly," filed on Oct. 4, 2016, published as U.S. Pub. No. 2017/0105757 on Apr. 20, 2017, issued as U.S. Pat. No. 10,987,123 on Apr. 27, 2021, the disclosure of which is incorporated by reference herein. Various suitable ways in which the teachings herein may be combined with the teachings of U.S. patent application Ser. No. 15/284,819, published as U.S. Pub. No. 2017/0105757 on Apr. 20, 2017, issued as U.S. Pat. No. 10,987,123 on Apr. 27, 2021, will be apparent to those of ordinary skill in the art.

It should be understood that the various teachings herein may be readily combined with the various teachings of U.S. patent application Ser. No. 15/284,837, entitled "Surgical Instrument with Dual Mode End Effector and Compound Lever with Detents," filed on Oct. 4, 2016, published as U.S. Pub. No. 2017/0105755 on Apr. 20, 2017, issued as U.S. Pat. No. 11,020,200 on Jun. 6, 2021, the disclosure of which is incorporated by reference herein. Various suitable ways in which the teachings herein may be combined with the teachings of U.S. patent application Ser. No. 15/284,837, published as U.S. Pub. No. 2017/0105755 on Apr. 20, 2017, issued as U.S. Pat. No. 11,020,200 on Jun. 6, 2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An ultrasonic surgical instrument, comprising:
    (a) an ultrasonic assembly comprising:
        (i) a body defining an arcuate channel,
        (ii) an acoustic waveguide secured relative to the body and extending along a longitudinal axis, and
        (iii) an ultrasonic blade extending distally from the acoustic waveguide; and
    (b) a clamp arm assembly coupled to the ultrasonic assembly and at least partially positioned along the longitudinal axis, wherein the clamp arm assembly comprises:
        (i) a clamp arm,
        (ii) a clamp arm actuator having a protrusion located thereon, and
        (iii) a linkage assembly, wherein the linkage assembly is configured to pivotally couple the clamp arm actuator and the clamp arm relative to the body such that the clamp arm actuator rotates toward and away from the body and the clamp arm rotates toward and away from the ultrasonic blade,
wherein the protrusion is sized to be received by the arcuate channel and the protrusion configured to prevent translation of the clamp arm relative to the ultrasonic assembly when the protrusion is received by the arcuate channel.

2. The ultrasonic surgical instrument of claim 1, wherein the linkage assembly includes a proximal pivot and a distal pivot, wherein the clamp arm actuator rotates about the proximal pivot to thereby pivot the clamp arm actuator toward and away from the body, wherein a distal portion of the clamp arm actuator transmits a rotational movement to a proximal portion of the clamp arm, wherein the clamp arm, in response to the rotational movement transmitted to the proximal portion of the clamp arm, rotates about the distal pivot to thereby drive the clamp arm toward and away from the ultrasonic blade.

3. The ultrasonic surgical instrument of claim 2, wherein the proximal pivot includes a boss that extends transversely relative to the longitudinal axis of the ultrasonic assembly through the clamp arm actuator.

4. The ultrasonic surgical instrument of claim 2, wherein the linkage assembly further includes an intermediate pivot positioned between the proximal pivot and the distal pivot, wherein the intermediate pivot rotatably couples the distal portion of the clamp arm actuator to the proximal portion of the clamp arm.

5. The ultrasonic surgical instrument of claim 4, wherein the intermediate pivot includes a pin and a slot, wherein the pin is positioned on one of the distal portion of the clamp arm actuator or the proximal portion of the clamp arm, and wherein the slot is positioned on the other of the distal portion of the clamp arm actuator or the proximal portion of the clamp arm.

6. The ultrasonic surgical instrument of claim 1, wherein the clamp arm actuator is pivotable toward and away from the body along a first path, wherein the clamp arm is pivotable toward and away from the body along a second path, wherein the first and second paths are on a same side of the longitudinal axis.

7. The ultrasonic surgical instrument of claim 1, wherein the clamp arm includes an upper tissue stop, wherein the upper tissue stop is configured to prevent a tissue from moving proximally when the tissue is clamped between the clamp arm and the ultrasonic blade.

8. The ultrasonic surgical instrument of claim 7, wherein the linkage assembly includes a linkage base, wherein the linkage base is configured to removably couple from the ultrasonic assembly.

9. The ultrasonic surgical instrument of claim 8, wherein the linkage base includes a channel configured to receive the ultrasonic blade therethrough.

10. The ultrasonic surgical instrument of claim 8, wherein the linkage base includes a lower tissue stop, wherein the lower tissue stop is configured to prevent the tissue from moving proximally when the tissue is clamped between the clamp arm and the ultrasonic blade.

11. A surgical instrument, comprising:
(a) a clamp arm assembly configured to removably couple with an ultrasonic assembly, wherein the clamp arm assembly comprises:
(i) a linkage base defining a longitudinal channel defining a longitudinal axis therealong, wherein the longitudinal channel is configured to receive the ultrasonic assembly,
(ii) a clamp arm, wherein the clamp arm is pivotally coupled to the linkage base at a distal pivot, wherein the clamp arm extends away from the longitudinal axis on a first side, and
(iii) a clamp arm actuator, having a protrusion located thereon, wherein the clamp arm actuator is pivotally coupled to the linkage base at a proximal pivot, wherein the clamp arm actuator is configured to be located on the first side of the longitudinal axis of the linkage base, wherein the clamp arm actuator is configured to pivot toward and away from the linkage base when the linkage base is coupled to the ultrasonic assembly to thereby pivot the clamp arm toward and away from the linkage base,
wherein the protrusion is sized to be received by an arcuate channel on the ultrasonic assembly, and the protrusion is configured to prevent translation of the clamp arm relative to the ultrasonic assembly when the protrusion is received by the arcuate channel.

12. The surgical instrument of claim 11, wherein the linkage base includes an intermediate pivot having an intermediate pin and a slot positioned between the proximal pivot and the distal pivot, wherein the intermediate pin is configured to pivotally mate with the slot, wherein one of the intermediate pin or the slot is configured to rotate the other of the slot or intermediate pin to pivotally move the clamp arm toward or away from the linkage base when the clamp arm or the clamp arm actuator is pivotally moved towards or away from the linkage base.

13. The surgical instrument of claim 11, wherein the clamp arm actuator includes an actuator Y-portion extending distally from a grip, wherein the actuator Y-portion rotatably couples to the proximal pivot.

14. The surgical instrument of claim 11, wherein the clamp arm includes a clamp arm Y-portion extending proximally from a clamp pad, wherein the clamp arm Y-portion rotatably couples to the distal pivot.

15. The surgical instrument of claim 11, wherein the ultrasonic assembly comprises:
(i) a body,
(ii) an acoustic waveguide secured relative to the body and configured to be positioned along the longitudinal axis, and
(iii) an ultrasonic blade extending distally from the acoustic waveguide.

16. The surgical instrument of claim 15, wherein the clamp arm includes a first tissue stop and the linkage base includes a second tissue stop, wherein the first and second tissue stops are configured to prevent a tissue from moving proximally when the ultrasonic assembly is coupled with the clamp arm assembly and the tissue is clamped between the clamp arm and the ultrasonic blade.

17. An ultrasonic surgical instrument, comprising:
(a) an ultrasonic assembly, wherein the ultrasonic assembly comprises:
(i) a body defining an arcuate channel,
(ii) an acoustic waveguide secured relative to the body and defining a longitudinal axis, and
(iii) an ultrasonic blade extending distally from the acoustic waveguide; and
(b) a clamp arm assembly, wherein the clamp arm assembly is configured to removably couple with the ultrasonic assembly, wherein the clamp arm assembly comprises:
(i) a clamp arm,
(ii) a clamp arm actuator having a protrusion thereon, and (iii) a linkage base, wherein the linkage base is configured to couple the clamp arm assembly to the ultrasonic assembly and pivotally couple the clamp arm to the clamp arm actuator, wherein the clamp arm actuator is configured to pivot toward and away from the body about the linkage base to thereby pivot the clamp arm toward and away from the ultrasonic blade when the ultrasonic assembly is coupled with the clamp arm assembly, wherein the protrusion is sized to be received by the arcuate channel on the ultrasonic assembly, and the protrusion is configured to prevent translation of the clamp arm relative to the ultrasonic assembly when the protrusion is received by the arcuate channel.

18. The ultrasonic surgical instrument of claim 17, wherein the linkage base includes a proximal pivot and a distal pivot, wherein the clamp arm actuator is pivotable about the proximal pivot to thereby pivot the clamp arm actuator toward and away from the body, wherein a distal portion of the clamp arm actuator rotatably moves a proximal portion of the clamp arm to thereby drive the clamp arm toward and away from the ultrasonic blade.

19. The ultrasonic surgical instrument of claim 18, further comprising an intermediate pivot wherein the intermediate pivot rotatably couples the proximal portion of the clamp arm to the distal portion of the clamp arm actuator, wherein the intermediate pivot is configured to transmit a rotational movement from the clamp arm actuator to the clamp arm.

20. The ultrasonic surgical instrument of claim 17, wherein the linkage base includes a tissue stop, wherein the tissue stop is configured to prevent a tissue from moving proximally when the tissue is clamped between the clamp arm and the ultrasonic blade.

* * * * *